(12) United States Patent
Eastlack et al.

(10) Patent No.: US 11,491,026 B2
(45) Date of Patent: Nov. 8, 2022

(54) METHODS AND APPARATUS FOR IMPLANTING AN INTERBODY DEVICE

(71) Applicant: Spine Innovation, LLC, Del Mar, CA (US)

(72) Inventors: Robert Eastlack, San Diego, CA (US); James Bruffey, San Diego, CA (US); Maneesh Bawa, San Diego, CA (US); Brian Bowman, Carlsbad, CA (US); Benjamin Arnold, San Diego, CA (US); Jude Paganelli, San Diego, CA (US); Urs Weber, Irvine, CA (US)

(73) Assignee: Spine Innovation, LLC, Del Mar, CA (US)

( * ) Notice: Subject to any disclaimer, the term of this patent is extended or adjusted under 35 U.S.C. 154(b) by 209 days.

(21) Appl. No.: 16/678,392

(22) Filed: Nov. 8, 2019

(65) Prior Publication Data
US 2020/0069435 A1 Mar. 5, 2020

Related U.S. Application Data

(60) Division of application No. 16/001,917, filed on Jun. 6, 2018, now Pat. No. 10,512,551, which is a
(Continued)

(51) Int. Cl.
*A61F 2/44* (2006.01)
*A61F 2/46* (2006.01)
*A61F 2/30* (2006.01)

(52) U.S. Cl.
CPC ............. *A61F 2/447* (2013.01); *A61F 2/442* (2013.01); *A61F 2/4455* (2013.01);
(Continued)

(58) Field of Classification Search
CPC .......... A61F 2/44; A61F 2/442; A61F 2/4425; A61F 2/4455; A61F 2/446; A61F 2/4465; A61F 2/447; A61F 2/4611
See application file for complete search history.

(56) References Cited

U.S. PATENT DOCUMENTS 6,039,761 A 3/2000 Li et al.
6,395,031 B1 5/2002 Foley et al.
(Continued)

FOREIGN PATENT DOCUMENTS

JP 2002528223 A 9/2002
WO WO-2012047712 A1 4/2012
(Continued)

OTHER PUBLICATIONS

European search report and search opinion dated Apr. 5, 2017 for EP Application No. 14819704.9.
(Continued)

*Primary Examiner* — Si Ming Ku
(74) *Attorney, Agent, or Firm* — Acuity IP, LLC; Nathan S. Cassell

(57) ABSTRACT

An interbody implant comprises one or more elongate members that have superior and inferior surfaces with a height, and medial and lateral surfaces having a width. The height is set so the implant fits into the intervertebral space. The width is less than the height. The interbody implant has a first configuration, a second configuration, and a third configuration. The interbody implant is inserted into the intervertebral space in the first configuration such that medial and lateral surfaces contact the vertebral bodies, and the interbody implant is then actuated into the second configuration such that superior and inferior surfaces engage the vertebral bodies. Actuation of the implant from the first configuration to the second configuration distracts the vertebral bodies. The implant is actuated into the third configu-
(Continued)

ration where the width of the implant is greater than width of the implant in the first or the second configuration.

10 Claims, 36 Drawing Sheets

Related U.S. Application Data continuation of application No. 14/322,702, filed on Jul. 2, 2014, now Pat. No. 10,265,192.

(60) Provisional application No. 61/842,888, filed on Jul. 3, 2013.

(52) U.S. Cl.
CPC ....... *A61F 2/4611* (2013.01); *A61F 2002/305* (2013.01); *A61F 2002/30019* (2013.01); *A61F 2002/3052* (2013.01); *A61F 2002/30176* (2013.01); *A61F 2002/30387* (2013.01); *A61F 2002/30471* (2013.01); *A61F 2002/30481* (2013.01); *A61F 2002/30492* (2013.01); *A61F 2002/30522* (2013.01); *A61F 2002/30537* (2013.01); *A61F 2002/30545* (2013.01); *A61F 2002/30563* (2013.01); *A61F 2002/30579* (2013.01); *A61F 2002/30593* (2013.01); *A61F 2002/30599* (2013.01); *A61F 2002/30601* (2013.01); *A61F 2002/30624* (2013.01); *A61F 2002/30828* (2013.01)

(56) References Cited

U.S. PATENT DOCUMENTS

| | | | |
|---|---|---|---|
| 6,833,066 B2 | 12/2004 | Baumann et al. | |
| 7,655,042 B2 | 2/2010 | Foley et al. | |
| 7,870,905 B2 | 1/2011 | Hermes et al. | |
| 7,993,403 B2 | 8/2011 | Foley et al. | |
| 8,317,866 B2 | 11/2012 | Palmatier et al. | |
| 10,265,192 B2 | 4/2019 | Eastlack et al. | |
| 10,512,551 B2 | 12/2019 | Eastlack et al. | |
| 2004/0002708 A1* | 1/2004 | Ritland | A61B 17/7011 606/254 |
| 2007/0219634 A1 | 9/2007 | Greenhalgh et al. | |
| 2008/0114367 A1 | 5/2008 | Meyer | |
| 2010/0106190 A1 | 4/2010 | Linares | |
| 2010/0145455 A1 | 6/2010 | Simpson et al. | |
| 2010/0185291 A1 | 7/2010 | Jimenez et al. | |
| 2010/0286783 A1 | 11/2010 | Lechmann et al. | |
| 2012/0083887 A1* | 4/2012 | Purcell | A61F 2/447 623/17.16 |
| 2012/0083889 A1 | 4/2012 | Purcell et al. | |
| 2012/0209386 A1 | 8/2012 | Triplett et al. | |
| 2012/0271422 A1 | 10/2012 | Miller et al. | |
| 2012/0310350 A1 | 12/2012 | Farris et al. | |
| 2013/0010315 A1 | 1/2013 | Yazawa et al. | |
| 2013/0103156 A1 | 4/2013 | Packer et al. | |
| 2013/0158668 A1 | 6/2013 | Nichols et al. | |

FOREIGN PATENT DOCUMENTS

| | | |
|---|---|---|
| WO | WO-2012135764 A1 | 10/2012 |
| WO | WO-2012047859 A2 | 10/2013 |
| WO | WO-2015003173 A2 | 1/2015 |

OTHER PUBLICATIONS

International search report and written opinion dated Feb. 10, 2015 for PCT Application No. US2014/045490.
Notice of allowance dated Sep. 27, 2019 for U.S. Appl. No. 16/001,917.
Office action dated Jan. 17, 2017 for U.S. Appl. No. 14/322,702.
Office action dated Jun. 11, 2019 for U.S. Appl. No. 16/001,917.
Office action dated Jul. 12, 2017 for U.S. Appl. No. 14/322,702.
U.S. Appl. No. 14/322,589, filed Jul. 2, 2014.
U.S. Appl. No. 14/322,702 Notice of Allowance dated Dec. 10, 2018.
U.S. Appl. No. 14/322,702 Office action dated Jul. 26, 2018.
U.S. Appl. No. 16/001,917 Office Action dated Jan. 31, 2019.
U.S. Appl. No. 16/001,917 Office Action dated Oct. 11, 2018.

* cited by examiner

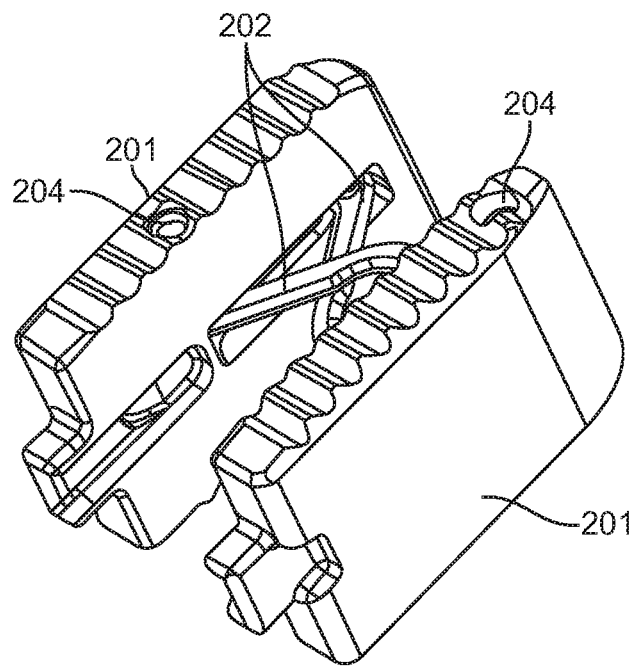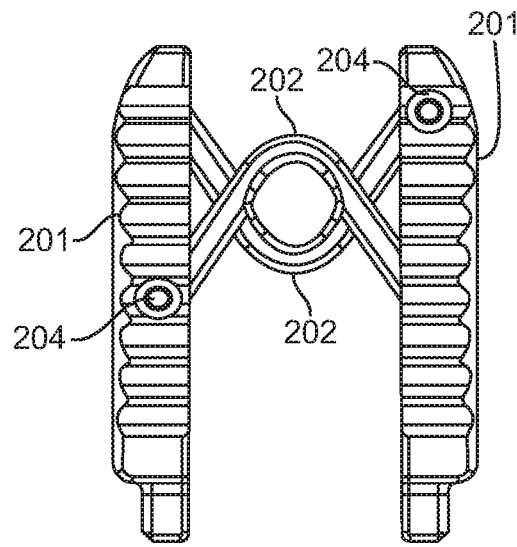
FIG. 21F  FIG. 21G
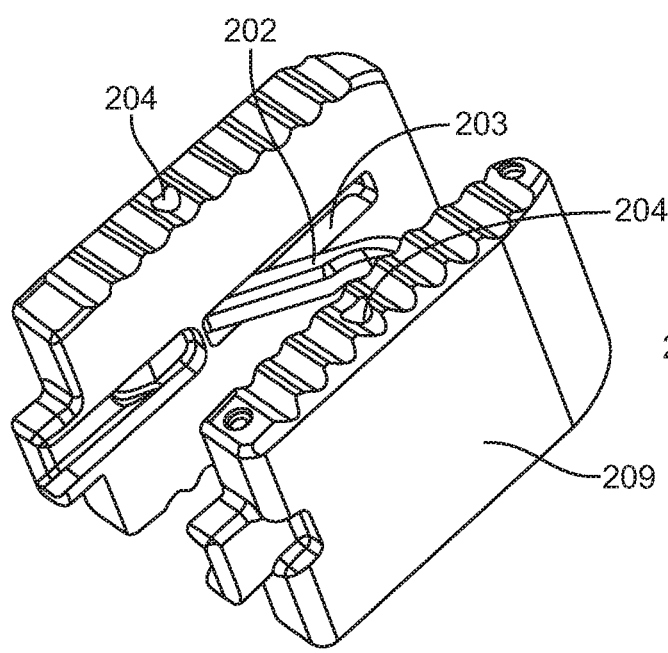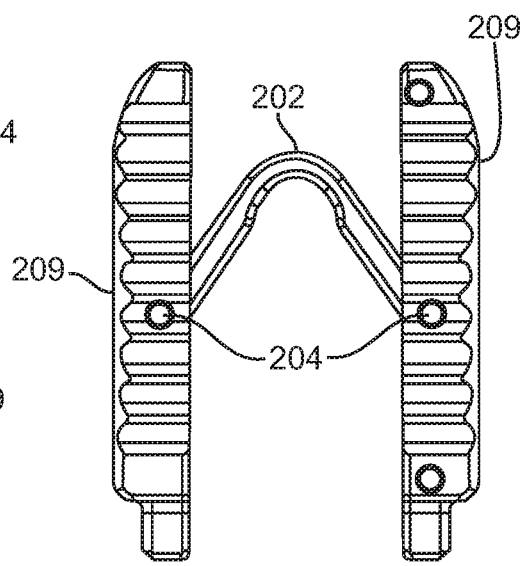
FIG. 22A  FIG. 22B

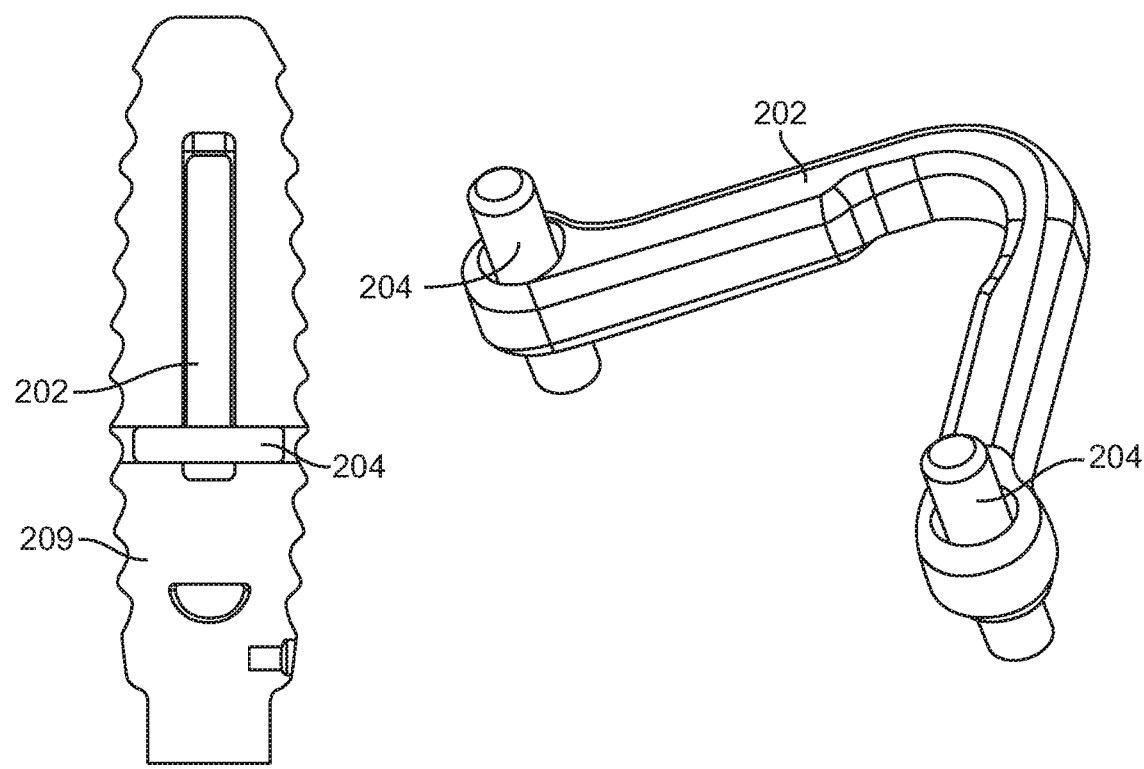
FIG. 22C
FIG. 22D
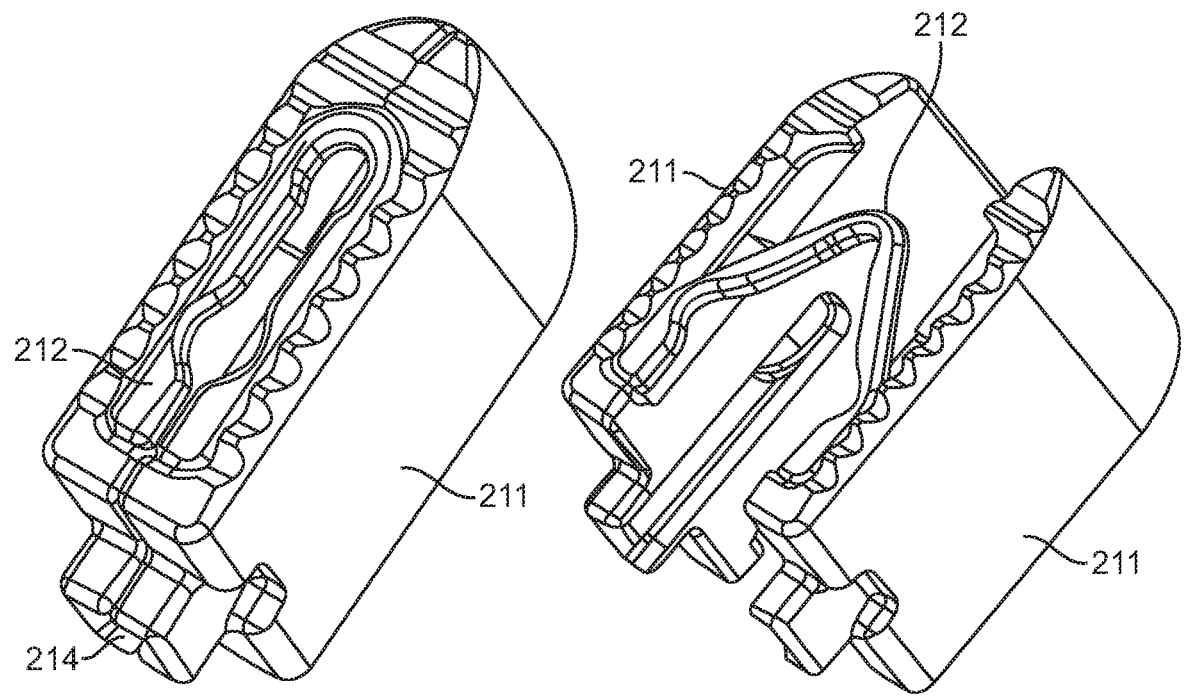
FIG. 23A
FIG. 23B

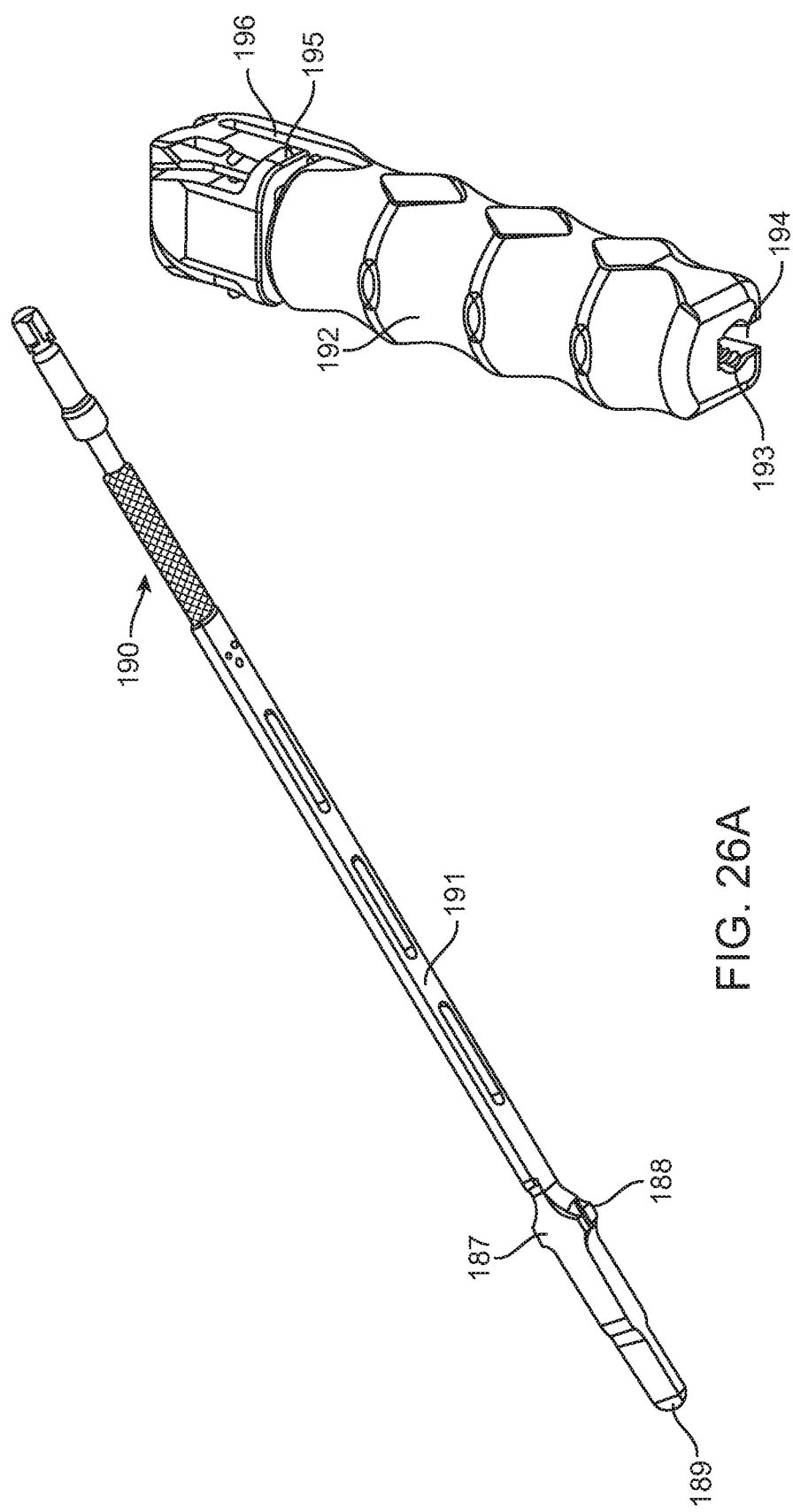

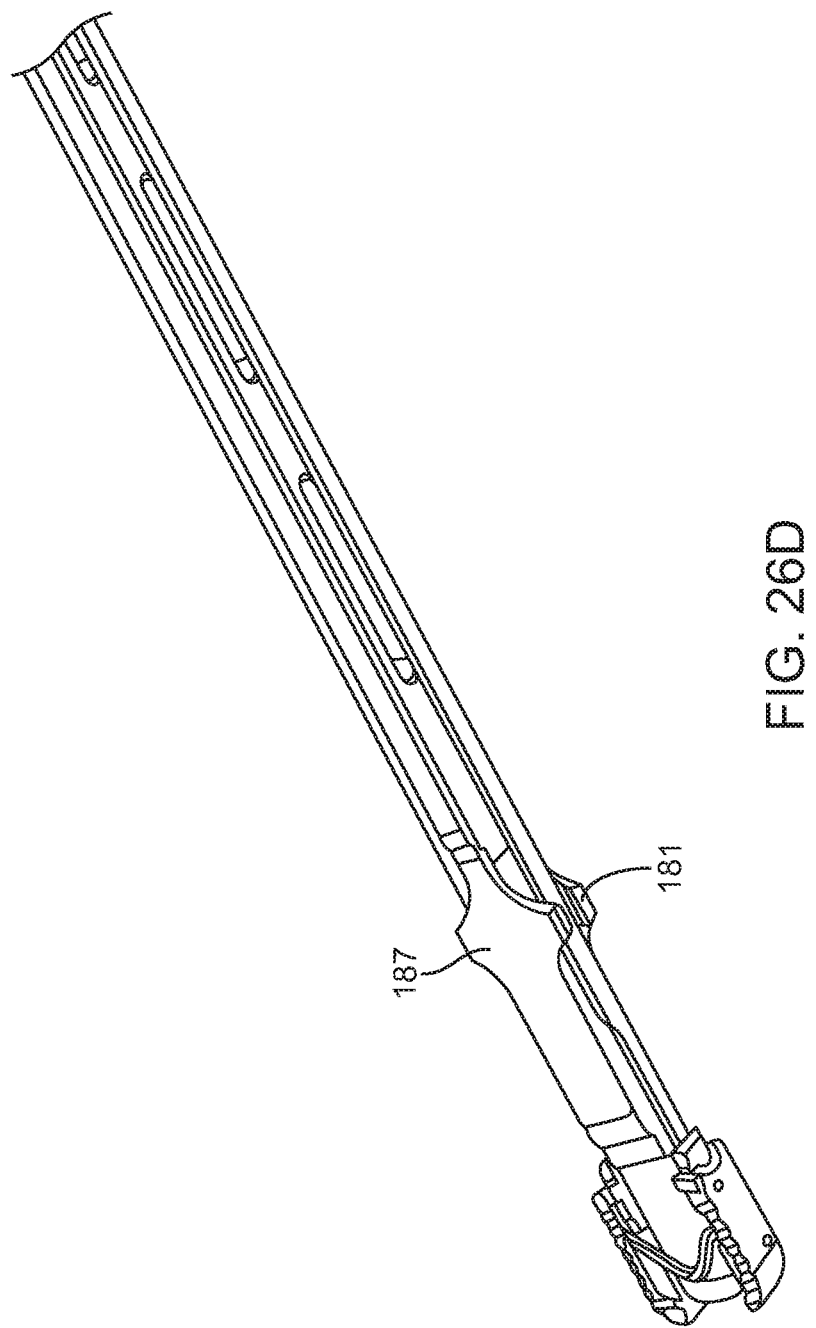

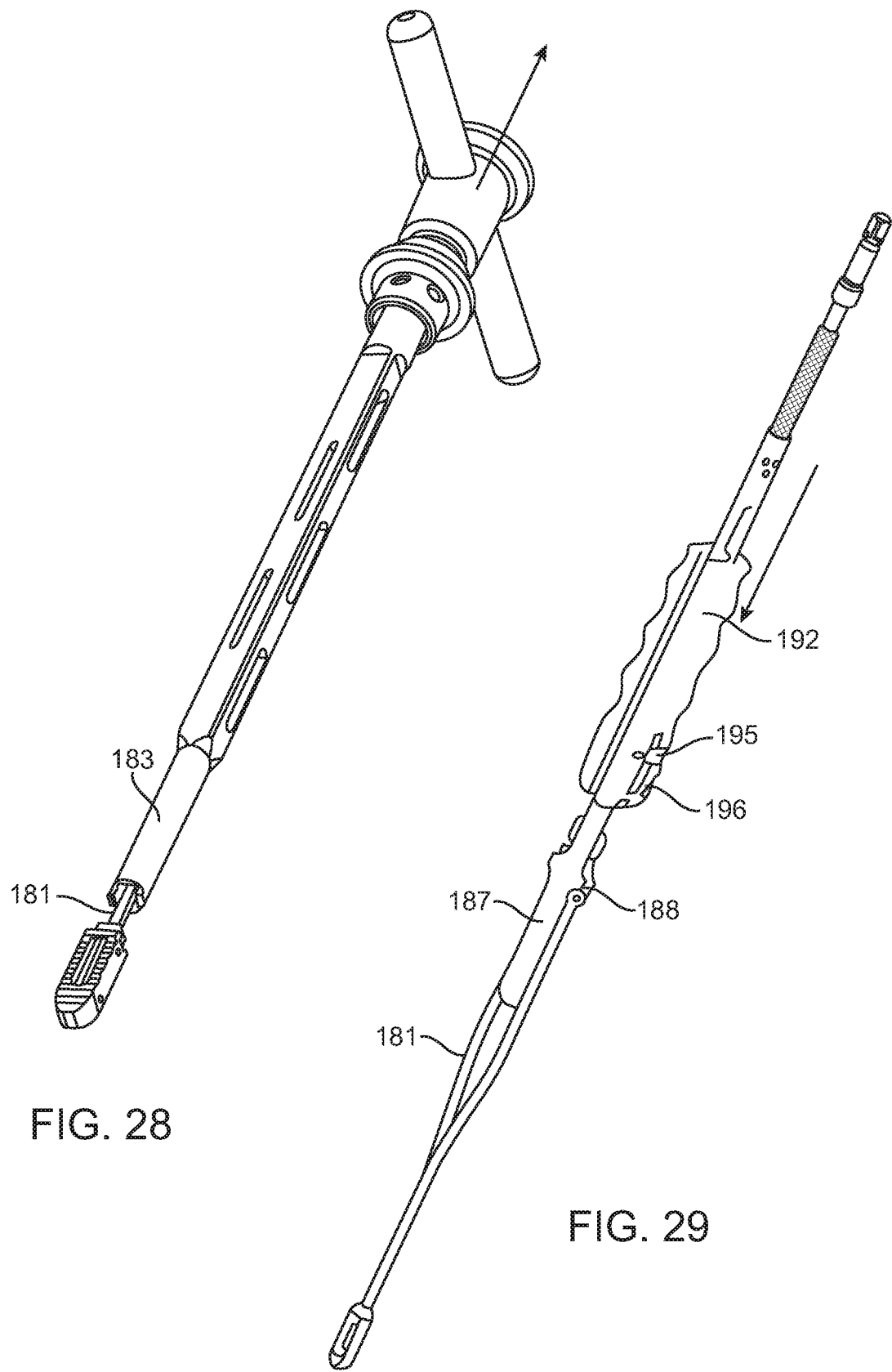

METHODS AND APPARATUS FOR IMPLANTING AN INTERBODY DEVICE

CROSS-REFERENCE

The present application is a divisional application of U.S. Non-Provisional patent application Ser. No. 16/001,917 filed on Jun. 6, 2018, which is a continuation application of U.S. Non-Provisional patent application Ser. No. 14/322,702 filed on Jul. 2, 2014, which is a non-provisional of, and claims the benefit of U.S. Provisional Patent Application No. 61/842,888 filed on Jul. 3, 2013; the entire contents of which are incorporated herein by reference.

The present application is related to U.S. patent application Ser. No. 14/322,589 filed Jul. 2, 2014; the entire contents of which are incorporated herein by reference.

BACKGROUND OF THE INVENTION

1. Field of the Invention. The present invention generally relates to medical devices and methods, and more particularly relates to interbody devices and methods of use. Interbody devices may be used for supporting and facilitating fusion of adjacent vertebrae in a patient's spine.

Various interbody fusion devices such as fusion cages may be implanted in the intervertebral disc space. These devices facilitate fusion of the adjacent vertebrae together and support the adjacent vertebral bodies. Depending on the size of the interbody fusion device and the corresponding delivery instrument, a surgeon may have to remove bone in order to provide adequate space. Clearly, it would be desirable if bone removal could be minimized or eliminated all together. Moreover, adjacent tissue may also need to be retracted or removed, and it would be desirable to minimize or eliminate this as well. Also, insertion of the implant often requires distraction of the vertebrae, therefore it would be desirable to provide a low profile implant that minimizes the amount of distraction required.

Newer interbody fusion devices are being developed which have a smaller more compact profile for delivery and a larger expanded profile after deployment. The smaller delivery size facilitates delivery, and the larger deployed configuration facilitates support and fusion of the bone. Therefore, it would be desirable to provide an interbody device that has an even smaller profile for delivery, and an even larger profile after implantation into the intervertebral disc space. At least some of these objectives will be satisfied by the devices and methods disclosed below.

2. Description of the Background Art. The following US patents and patent publications are related to interbody devices: 2013/0103156; 2012/0083887; 2012/0083889; 2012/0310350; 8,317,866; 7,870,905; 6,395,031; 6,833,066; 7,655,042; and 7,993,403.

SUMMARY OF THE INVENTION

The present invention generally relates to medical devices and methods, and more particularly relates to interbody devices and methods of use. Interbody devices may be used for supporting and facilitating fusion of adjacent vertebrae in a patient's spine.

In a first aspect of the present invention, an interbody implant for implanting in an intervertebral space surrounded by adjacent vertebral bodies in a patient during spinal fusion comprises one or more elongate members that form the implant. The one or more elongate members have superior and inferior surfaces with a height therebetween, and medial and lateral surfaces with a width therebetween. The superior and inferior surfaces are shaped to engage the vertebral bodies, and the height is set at a predetermined distance that is sized to fit into the intervertebral space. The width is set at a predetermined distance less than the predetermined height. The interbody implant has a first configuration, a second configuration, and a third configuration. The interbody implant is inserted into the intervertebral space in the first configuration such that medial and lateral surfaces contact the vertebral bodies. The interbody implant is actuated into the second configuration such that superior and inferior surfaces engage the vertebral bodies, and actuation of the implant from the first configuration to the second configuration distracts the vertebral bodies away from one another to increase the intervertebral space. The implant is actuated into the third configuration where the width of the implant is greater than width of the implant in the first or the second configuration.

The second configuration may have the same width and height as the first configuration. The one or more elongate members may comprise two elongate members, and actuation of the implant from the second configuration to the third configuration may be obtained by translation of the two elongate members away from one another. The two elongate members may be coupled together with one or more spanning components that deform between the second and the third configurations.

The two elongate members may be coupled together with one or more spanning components, and the two elongate members may translate along the one or more spanning components. The one or more spanning components may comprise a first spanning component and a second spanning component. The first spanning component may face in a first direction, and the second spanning component may face in a second direction opposite the first direction. The first spanning component may be disposed over the second spanning component. The one or more spanning components may be at least partially disposed in a recessed region of the one or more elongate members. At least one of the one or more spanning components may comprise a first arm and a second arm. Each arm may have a free end and a hinged end. The hinged ends may be coupled together with a hinge. Each arm may further comprise a supplemental hinge disposed between the free end and the hinged end. The supplemental hinge may be configured to allow the free end to bend independently of the hinged end. At least one of the one or more spanning components may comprise one or more apertures disposed in an arm of the spanning component. The one or more apertures may be sized to receive a pin. The one or more spanning component may consist of only one spanning component.

The one or more spanning components may comprise a locking feature, and the two elongate members may lock into the third configuration when the two elongate members engage the locking feature. The one or more spanning components may comprise a plurality of assembled components configured to telescope over one another thereby allowing the two elongate members to translate relative to one another. The one or more elongate members may comprise an engagement feature configured to allow the one or more elongate members to be releasably coupled to an insertion instrument, and the insertion instrument may be actuatable. Actuation of the insertion instrument may actuate the implant from the second configuration to the third configuration.

The one or more elongate members may comprise a first elongate member and a second elongate member. The implant may further comprise a posterior cap that is engaged with the first and second elongate members and that is configured to hold the elongate members in the third configuration. At least some of the superior or inferior surfaces of the one or more elongate members may comprise anti-migration teeth.

In another aspect of the present invention, an interbody implant for implanting in an intervertebral space surrounded by adjacent vertebral bodies in a patient during spinal fusion comprises a plurality of elongate members that form the implant, and one or more spanning members that are coupled with the plurality of elongate members. The plurality of elongate members have superior and inferior surfaces with a height therebetween, and medial and lateral surfaces have a width therebetween. The superior and inferior surfaces are shaped to engage the vertebral bodies, and the height is set at a predetermined distance that is sized to fit into the intervertebral space. The width is set at a predetermined distance less than the predetermined height. The interbody implant has a first configuration, a second configuration, and a third configuration. The interbody implant is inserted into the intervertebral space in the first configuration such that medial and lateral surfaces contact the vertebral bodies, and the interbody implant is actuated into the second configuration such that the superior and inferior surfaces engage the vertebral bodies and distract the vertebral bodies away from one another. In the third configuration the width is greater than the width in the first or the second configuration, and actuation from the second configuration to the third configuration comprises translation of the one or more elongate members laterally away from one another.

The plurality of elongate members may be coupled together with the one or more spanning members and that may deform between the second and third configurations. The one or more spanning components may comprise a first spanning and a second spanning component. The first spanning component may face in a first direction, and the second spanning component may face in a second direction opposite the first direction. The first spanning component may be disposed over the second spanning component. The one or more spanning components may be at least partially disposed in a recessed region of the one or more elongate members. At least one of the one or more spanning components may comprise a first arm and a second arm. Each arm may have a free end and a hinged end. The hinged ends are coupled together with a hinge. Each arm may also comprise a supplemental hinge disposed between the free end and the hinged end. The supplemental hinge may be configured to allow the free end to bend independently of the hinged end. AT least one of the one or more spanning components may comprise one or more apertures disposed in an arm of the spanning component, and the aperture may be sized to receive a pin. The one or more spanning components may consist of only one spanning component.

The plurality of elongate members may be coupled together with the one or more spanning components, and the plurality of elongate members may translate along the one or more spanning components. The one or more spanning members may comprise locking features, and the plurality of elongate members may lock into the third configuration when the plurality of elongate members engage the locking features. The one or more spanning members may comprise a plurality of assembled components configured to telescope over one another thereby allowing the plurality of elongate members to translate relative to one another. The plurality of elongate members may comprise an engagement feature configured to allow the plurality of elongate members to be releasably coupled to an insertion instrument. The insertion instrument may be actuatable and wherein actuation of the insertion instrument may actuate the implant from the second configuration to the third configuration.

The plurality of elongate members may comprise a first elongate member and a second elongate member. The implant may further comprise a posterior cap that is engaged with the first and second elongate members and the cap may be configured to hold the elongate members in the third configuration. At least some of the superior or inferior surfaces of the plurality of elongate members comprise anti-migration teeth.

In yet another aspect of the present invention, a method for delivering an interbody implant into an intervertebral space of a patient comprises inserting an interbody implant into the intervertebral space in a first configuration, actuating the interbody implant from the first configuration to a second configuration such that the interbody implant distracts the intervertebral space to a greater height when the interbody implant is in the second configuration, and actuating the interbody implant from the second configuration to a third configuration, wherein in the third configuration implant width increases relative to width of the implant in the first configuration.

Actuating the interbody implant from the first configuration to the second configuration may comprise rotating the interbody implant in the intervertebral space. Actuating the interbody implant from the second configuration to the third configuration may comprise expanding two or more elongate members away from one another. Expanding the two or more elongate members may comprise expanding two elongate members away from one another and the two expanded elongate members may remain substantially parallel with one another after expansion. The method may further comprise locking the interbody implant in the third configuration. Locking the interbody implant may comprise engaging a cap against a posterior portion of the interbody implant. Actuating the interbody implant from the second configuration to the third configuration may comprise actuating an expansion instrument. The expansion instrument may comprise a wedged tip and actuating the interbody implant may comprise inserting the wedged tip into the interbody implant thereby causing expansion of the interbody implant. The interbody implant may be coupled to a delivery instrument and the method may further comprise releasing the interbody implant from the delivery instrument. The first configuration may comprise a collapsed configuration and inserting the interbody implant into the intervertebral space in the collapsed configuration may comprise coupling the interbody implant with an elongate shim, coupling the elongate shim with an insertion instrument, advancing the insertion instrument toward the intervertebral space, and disposing the interbody implant in the intervertebral space. Actuating the interbody implant from the first configuration to the second configuration may comprise rotating the insertion instrument thereby rotating the interbody implant. Actuating the interbody implant from the second configuration to the third configuration may comprise uncoupling the insertion instrument from the elongate shim, coupling an expansion instrument with the elongate shim, and advancing a wedged portion of the expansion instrument into the interbody implant thereby expanding the interbody implant.

In still another aspect of the present invention, a system for delivering an interbody implant into an intervertebral space of a patient, comprises an interbody fusion device and an elongate shim having a proximal end and a distal end, wherein the distal end comprises an engagement element for releasably coupling the interbody fusion device. The proximal end is configured to engage a surgical instrument.

The interbody fusion device may comprise a receptacle having a shoulder, and the engagement element comprises an angled protrusion with a flat shoulder, the angled protrusion configured to be advanced into the receptacle in the interbody fusion device and the flat shoulder of the engagement element engages the shoulder of the receptacle. The system may further comprise an insertion instrument having an elongate shaft with a central channel therethrough and a handle disposed on a proximal portion of the elongate shaft. The central channel may be sized to receive the elongate shim. The system may also comprise an expansion instrument having an elongate shaft and an expansion wedge near the distal portion of the elongate shaft. The expansion wedge may be configured to be advanced into the interbody fusion device thereby causing the interbody fusion device to expand. The expansion instrument may also have a proximal portion of the elongate shaft configured to be engaged with a handle.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 21A-21G illustrate perspective, partial cross-sectional, or top views of various aspects of other exemplary embodiments of the interbody fusion device.

FIGS. 22A-22D illustrate perspective, top or partial cross-sectional views of aspects of another exemplary embodiment of an interbody fusion device.

FIGS. 23A-23E illustrate perspective or top views of features of still another exemplary embodiment of an interbody fusion device.

FIGS. 26A-26E illustrate a perspective view of various features of several embodiments of an expansion tool.

FIG. 28 illustrates a perspective view of the removal of the insertion instrument from the implant.

FIG. 29 illustrates a perspective view of the engagement of expansion instrument with the implant.

DETAILED DESCRIPTION OF THE INVENTION

Specific embodiments of the disclosed device and method of use will now be described with reference to the drawings. Nothing in this detailed description is intended to imply that any particular component, feature, or step is essential to the invention.

Interbody Fusion Devices.

Figure 1:
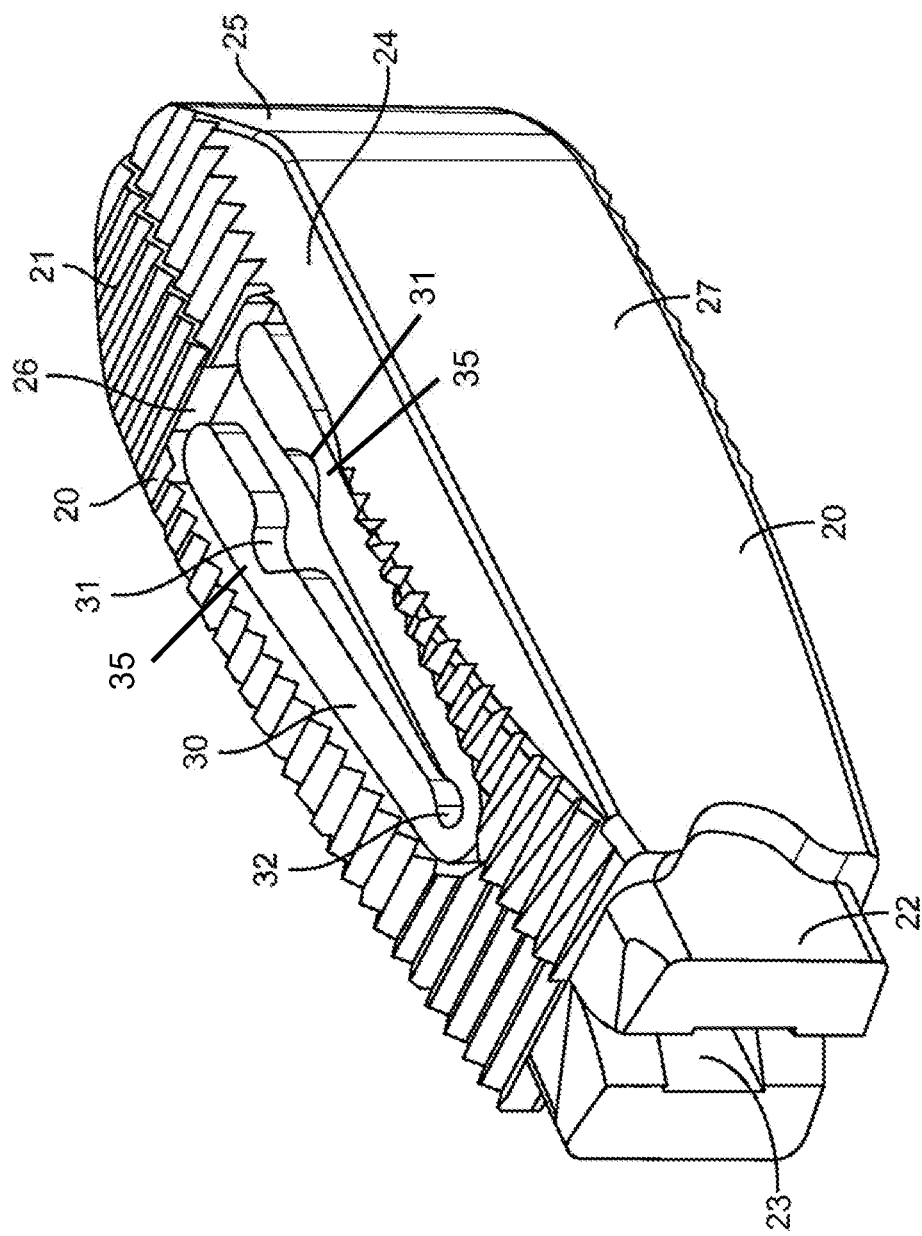
FIG. 1 is a perspective view of an exemplary embodiment of an interbody fusion device in the collapsed configuration.

FIG. 1 is a preferred embodiment of the interbody device (also referred to as the implant) where the elongated members 20 are connected by two spanning components 30. One is adjacent a superior surface of the interbody device and the other is adjacent the inferior surface of the interbody device. This embodiment is designed to be inserted into the disc space in one configuration with the smooth walls 27 contacting the endplates, rotated into a second configuration where the top and bottom surfaces 21 contact the endplates, and then expanded in width to a third configuration where the smooth walls 27 are at a greater distance apart than they are in the second configuration. The distance between the smooth walls 27 is less than the distance between the top and bottom surfaces 21 so that when the implant is rotated from the first configuration into the second configuration it distracts the disc space. In this embodiment of the implant, the spanning members are designed to deform during the width expansion so they have been made with deformation zone 31 of supplemental hinge 35 and deformation zone 32 of hinge. The spanning components 30 fit into a recessed pocket 26 that is formed in the top or bottom surfaces 21 of the elongated members 20 when they are in their collapsed state. The top and bottom surfaces 21 are equipped with anti-migration teeth that allow for translation of the elongated members 20 during width expansion but help to prevent translation of the device along the longitudinal axis of the elongated members 20. The elongated members have angled surfaces 25 that form a tapered end for easier introduction into the disc space. In order to aide in the rotation of the implant, two corners of the implant have been chamfered 24. In order to facilitate the insertion, rotation, and width expansion, of the implant, a slot 23 and a rectangular end 22 are designed to mate with an insertion instrument.

Figure 2:
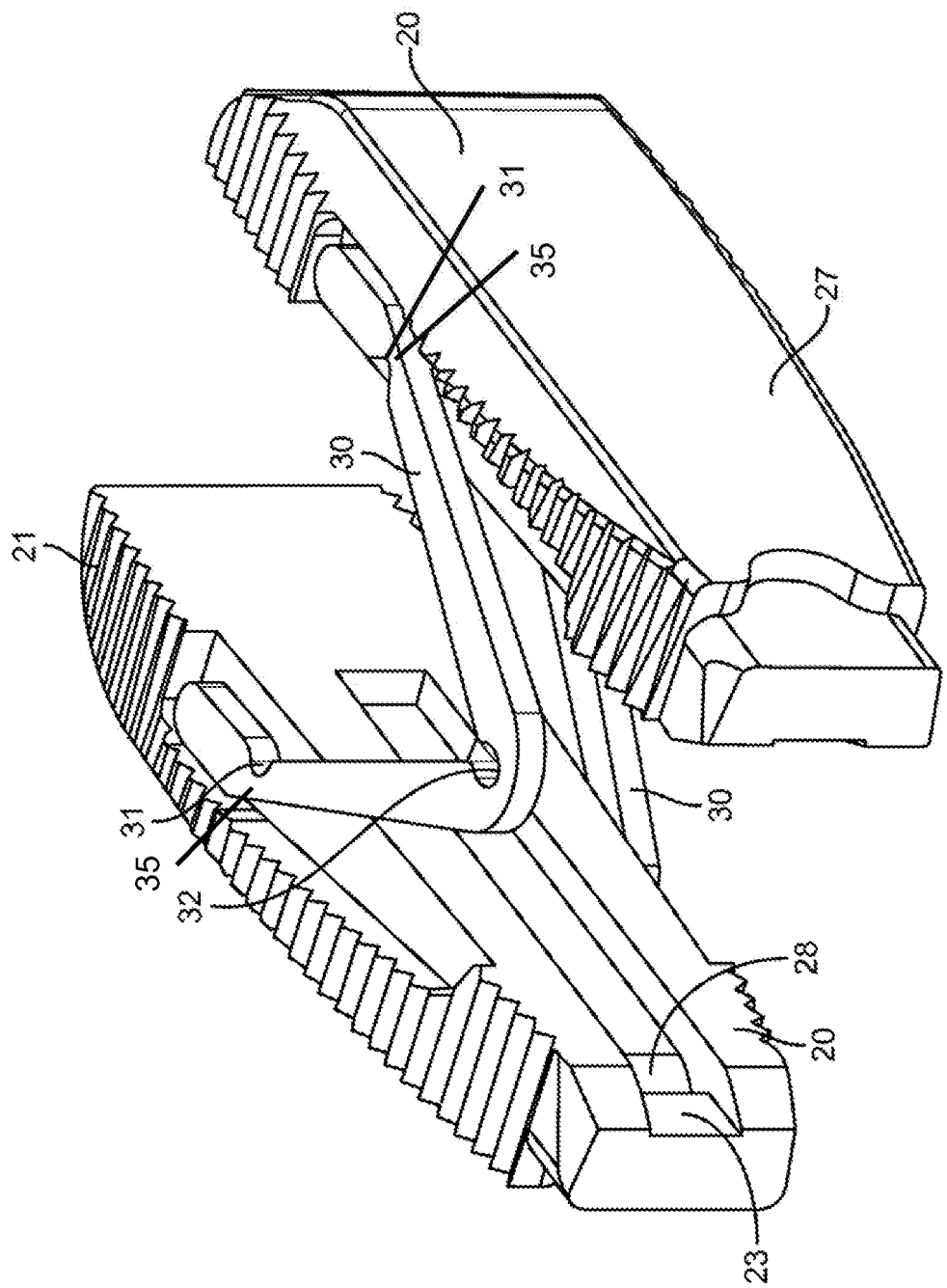
FIG. 2 is a perspective view of the embodiment in FIG. 1 after it has been expanded.

FIG. 2 shows the implant in the expanded configuration with the elongated elements 20 translated relative to one another and the spanning components 30 in their deformed states with deformation having occurred at deformation zone 31 of supplemental hinge 35 and deformation zone 32 of hinge. The elongated elements 20 may be parallel with one another in the expanded configuration, or they may be transverse to one another. Also visible in FIG. 2 is notch 28 which is designed to engage with the insertion instrument.

Figure 3:
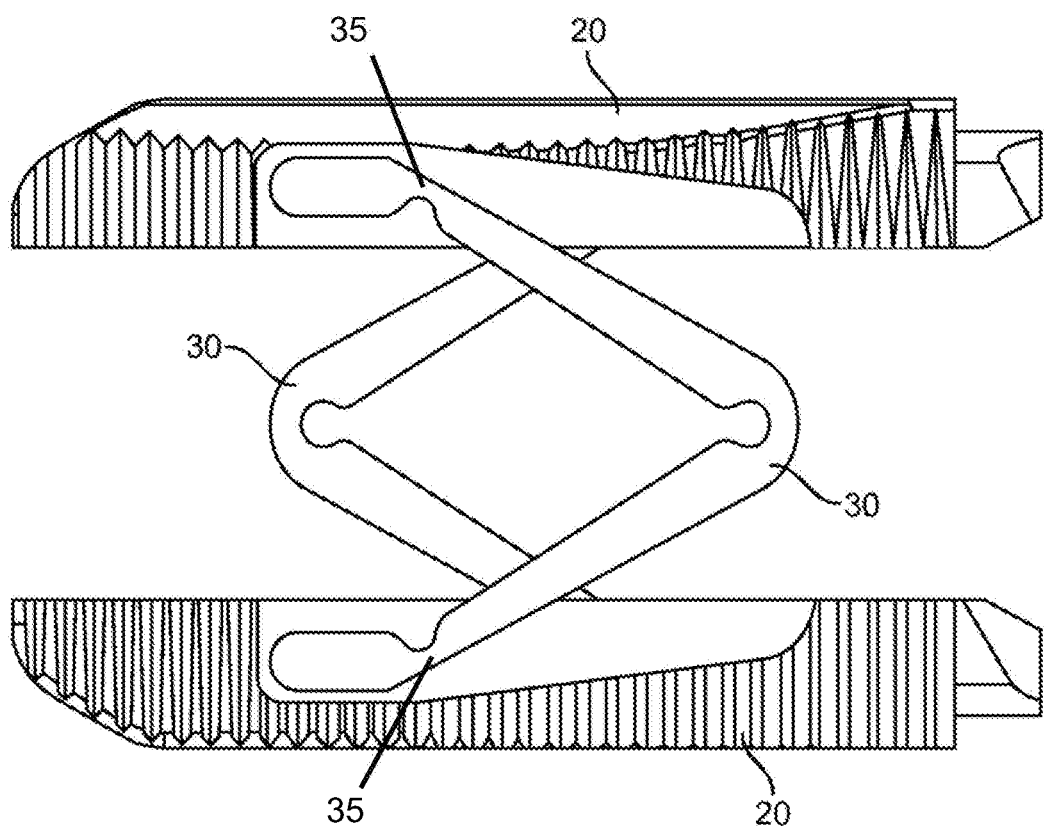
FIG. 3 is a top view of the embodiment in FIG. 2.

FIG. 3 is a top view of the implant in the expanded state with both elongated members and spanning components 30 clearly visible. The spanning components (also referred to herein as spanning members) 30 are positioned on opposite ends of one another and are configured in opposite directions for a uniform expansion. Therefore, in this embodiment one spanning component has first and second arms connected together with a hinge that opens up an forms an angle facing in one direction, and the other spanning component also has first and second arms that are connected together with a hinge that opens up and forms an angle facing in the opposite direction as the other spanning component.

Figure 4:
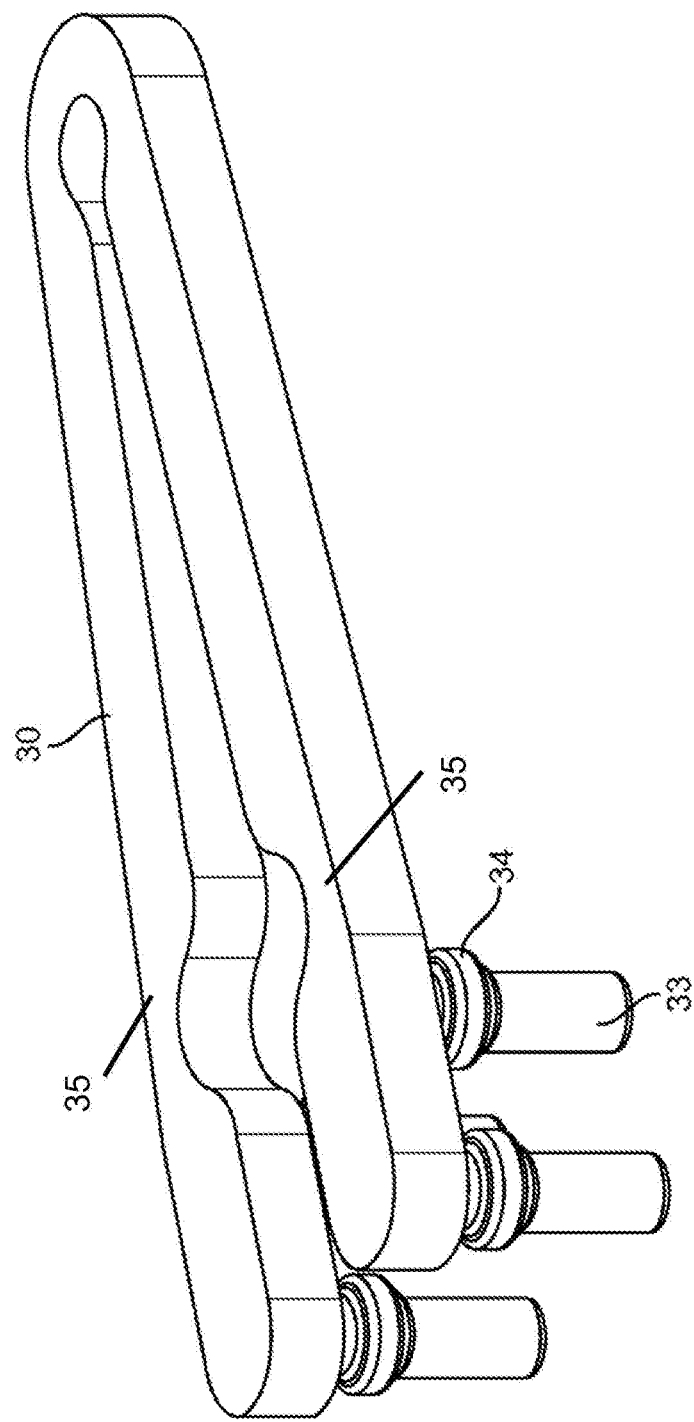
FIG. 4 illustrates a perspective view of a spanning component from the embodiment of FIG. 1.

FIG. 4 shows the spanning components separate from the implant. Four engagement pins 33 and snap features 34 are designed to attach the spanning components 30 to the elongated members 20.

Figure 5:
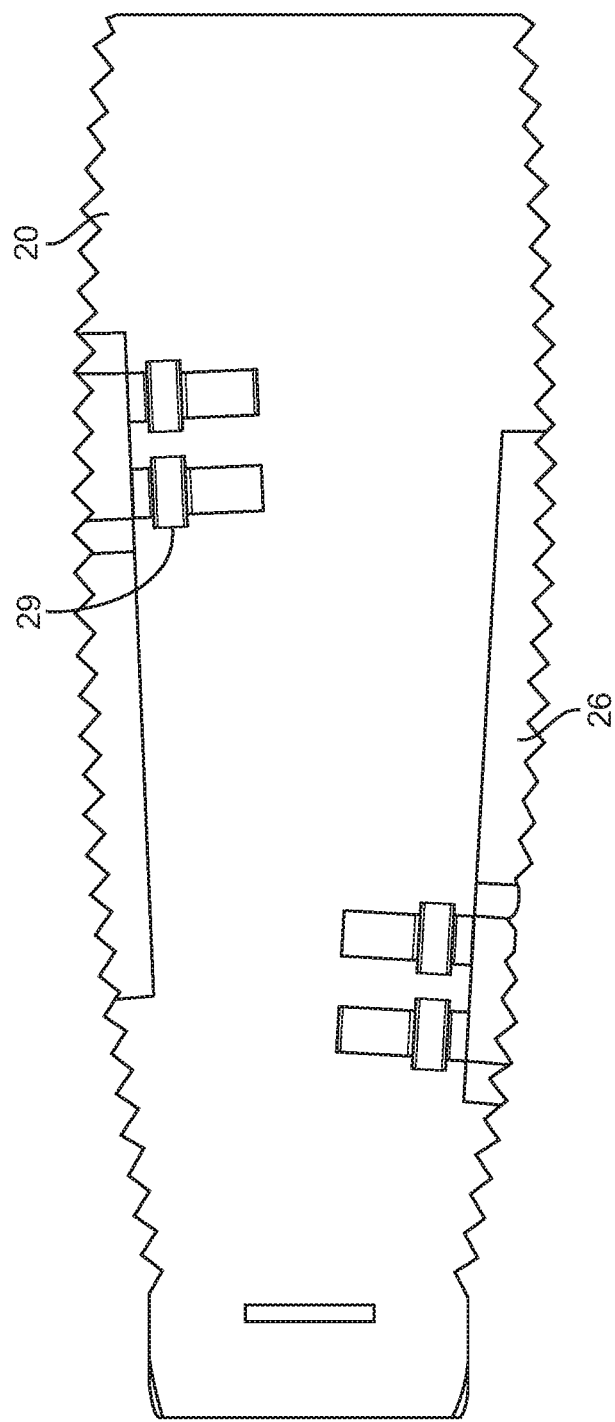
FIG. 5 illustrates a partial cross-section of the interbody fusion device in FIG. 1.

FIG. 5 shows a cross-section of the elongated member 20 where the attachment holes 29 that engage with the pins 33 and snap features 34 of the spanning members 30 are shown. Two pins on each arm of the spanning members are used in order to prevent unwanted pivoting at the connection point.

Figure 6:
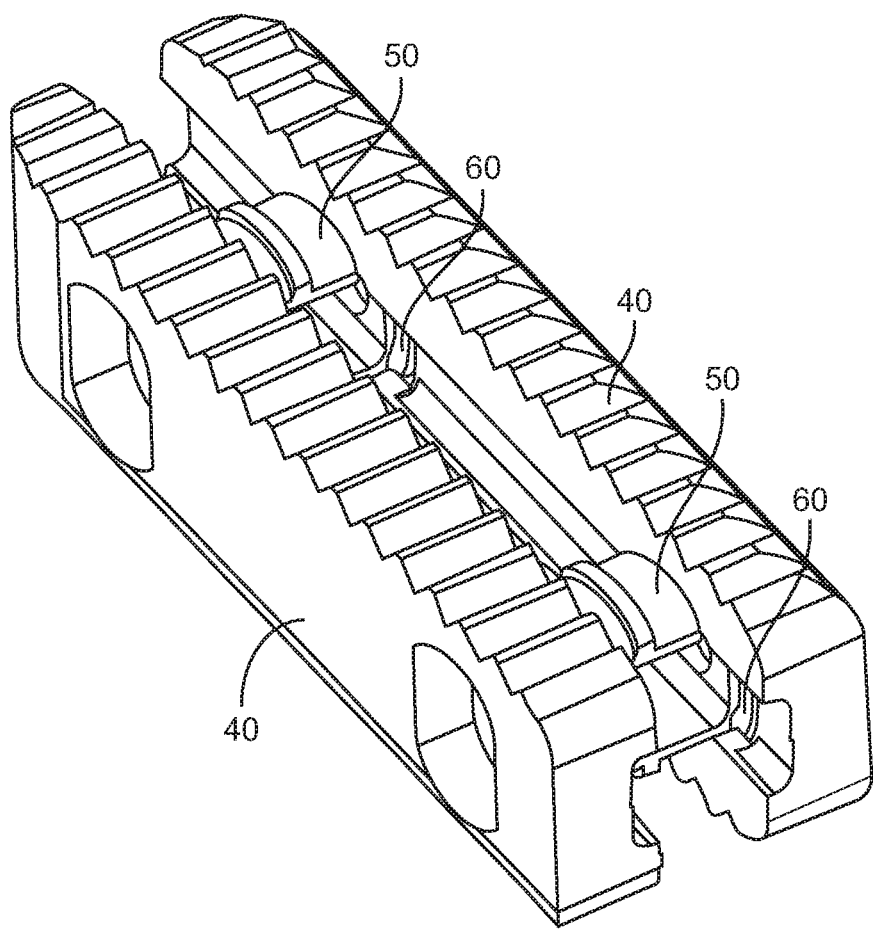
FIG. 6 illustrates a perspective view of another exemplary embodiment of an interbody fusion device.

FIG. 6 shows an additional embodiment of the implant where the elongated members 40 are attached with two spanning members 50 that lock the elongated members 40 in their expanded configuration via mating geometry in the both the spanning members 50 and the elongated members 40 and a set of c-clips 60 as will be described below.

Figure 7:
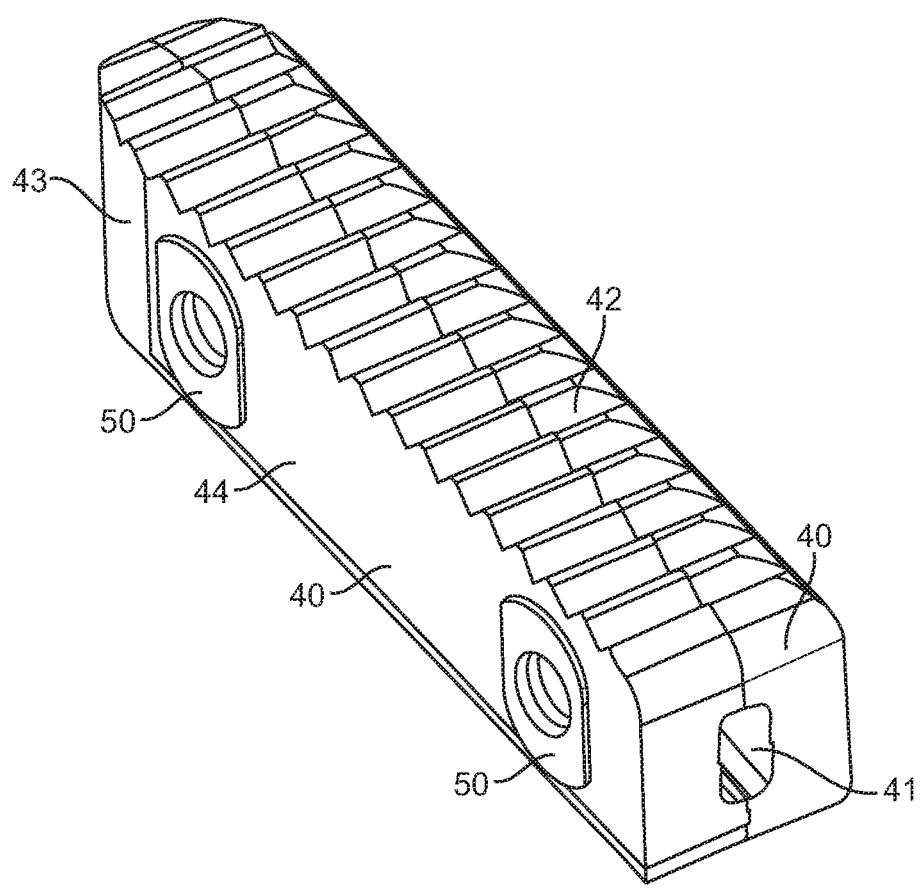
FIG. 7 illustrates a perspective view of the embodiment in FIG. 6 while in the collapsed configuration.

FIG. 7 shows the implant of FIG. 6 in its collapsed state with a tapered end 43, smooth side walls 40, top and bottom surfaces 42, and an instrument engagement feature 41. The tapered end 43 facilitates insertion into the intervertebral space.

Figure 8:
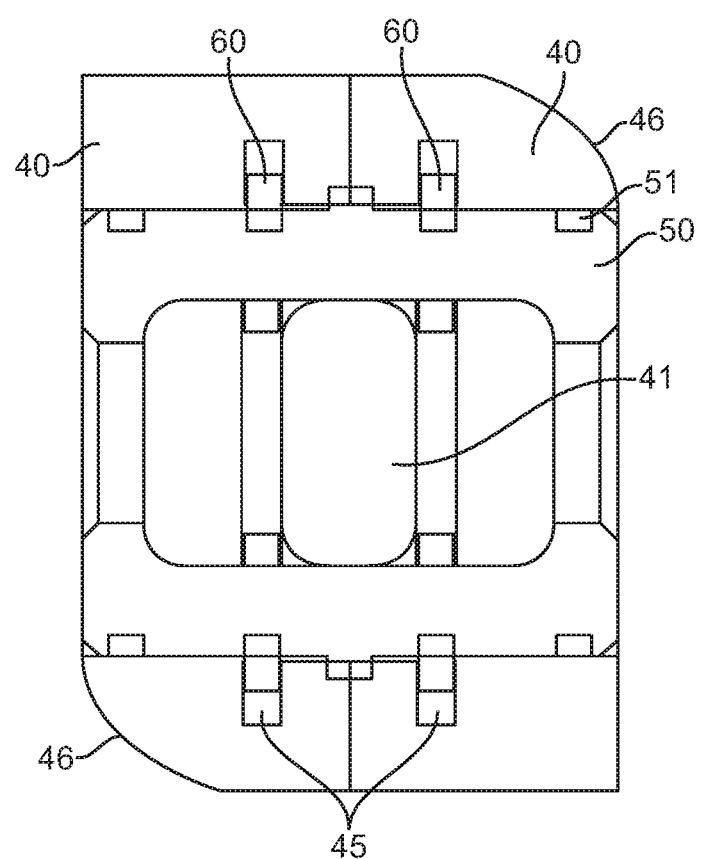
FIG. 8 illustrates a partial cross-section through the embodiment of FIG. 6.

In FIG. 8 a cross-section of FIG. 7 taken through the spanning member 50 and this view shows the elongated members 40 with pockets 45 for the c-clips 60 and the spanning member with locking grooves 51. In the expanded width the c-clips 60 lock into the locking grooves 51 on the spanning members 50. Thus, the c-clips expand and contract such that when they move into the locking grooves they prevent motion. Also visible in FIG. 8 are curved corners 46 that help facilitate the rotation from the first configuration to the second configuration.

Figure 9:
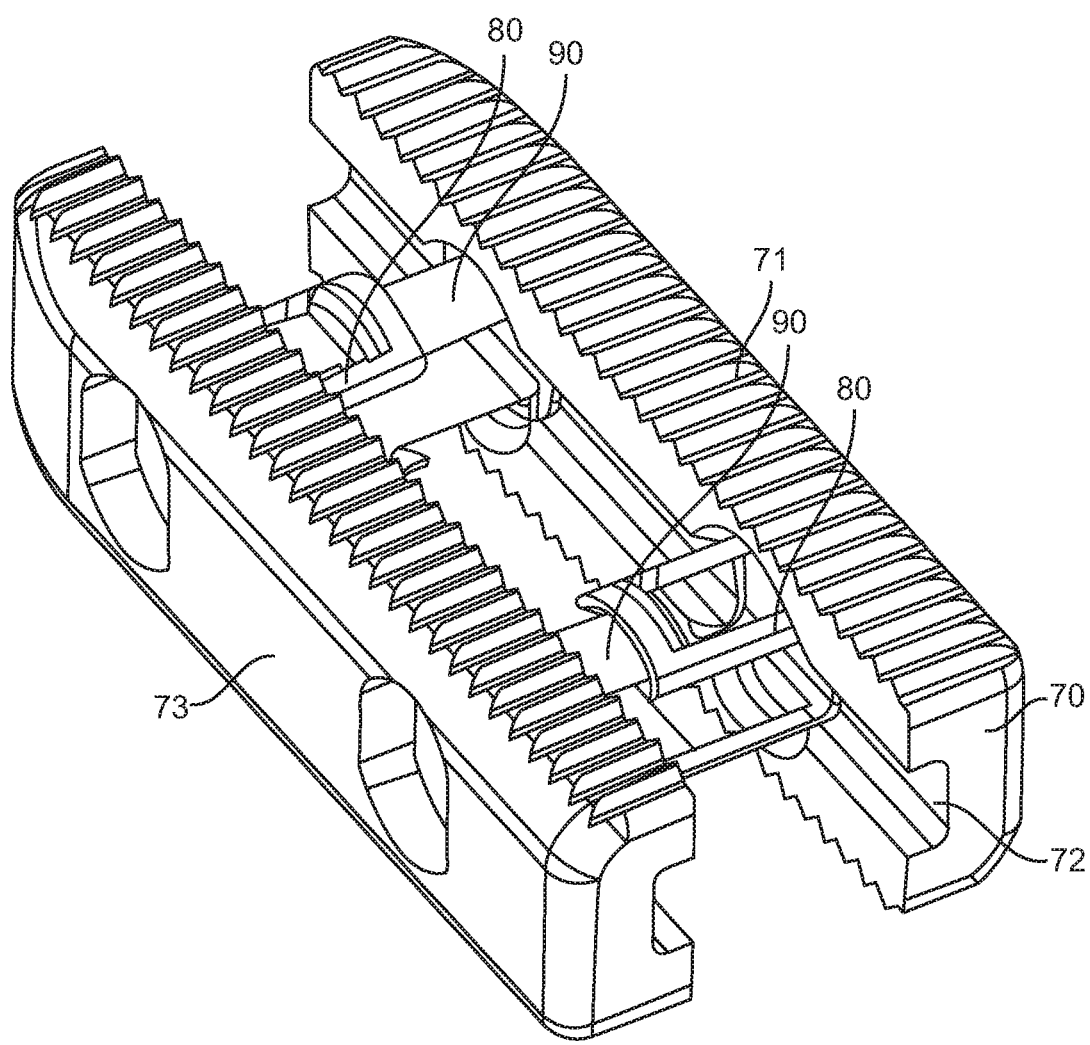
FIG. 9 illustrates a perspective view of another exemplary embodiment of an interbody fusion device in the expanded configuration.

FIG. 9 shows another exemplary embodiment of the implant where the spanning components 80 and 90 telescope relative to each other to allow for greater translation of the elongated members 70. FIG. 9 shows the device in its expanded state with smooth side walls 73, top and bottom surfaces 71, and instrument engagement feature 72.

Figure 10:
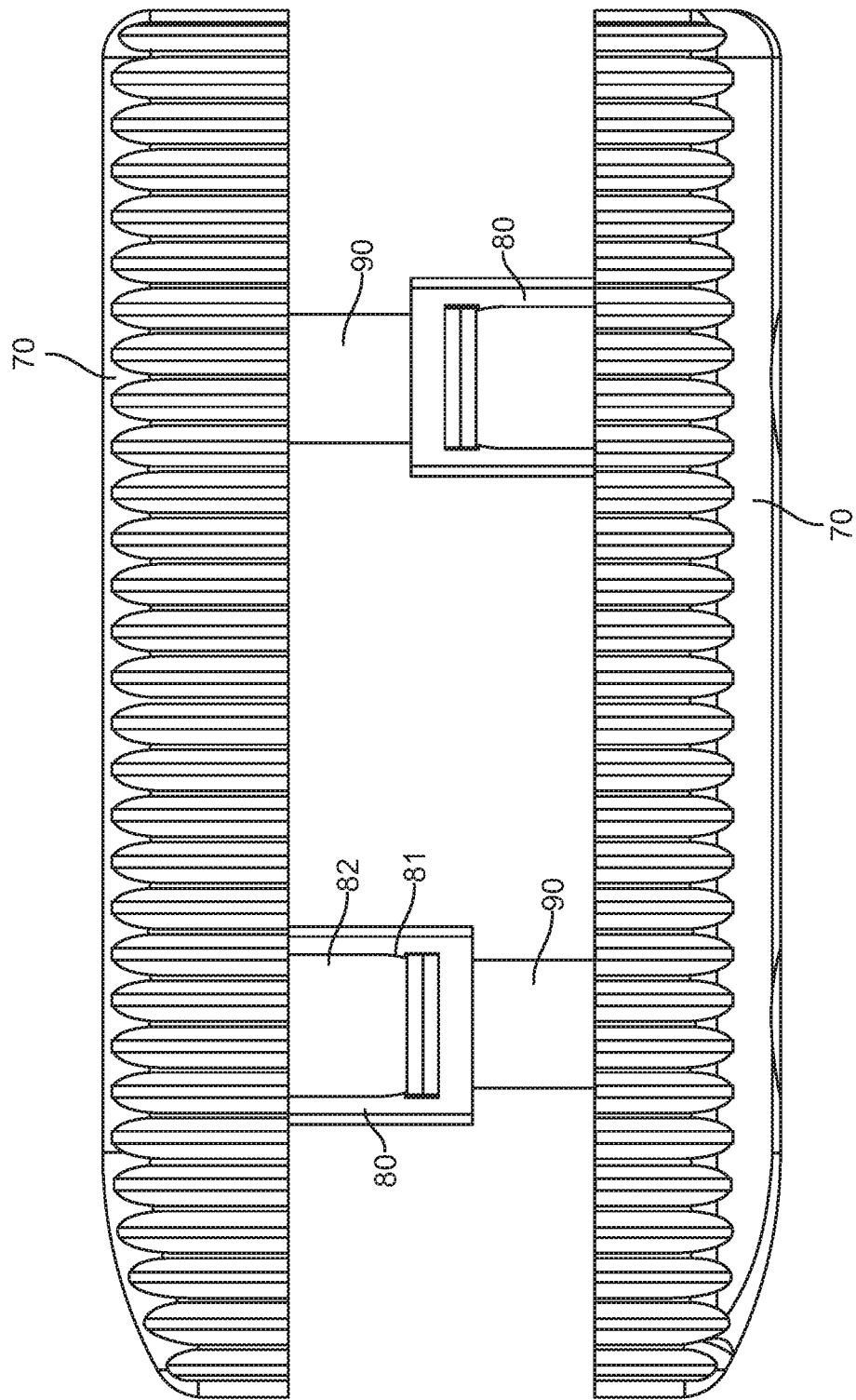
FIG. 10 is a top view of the embodiment in FIG. 9.

In FIG. 10 the embodiment of FIG. 9 is shown from a top view in the expanded state. Slot 82 in the first spanning component 80 allows for the telescoping of the second spanning component 90. Snap feature 81 locks the first spanning component 80 and the second spanning component 90 relative to one another when in the expanded state.

Figure 11:
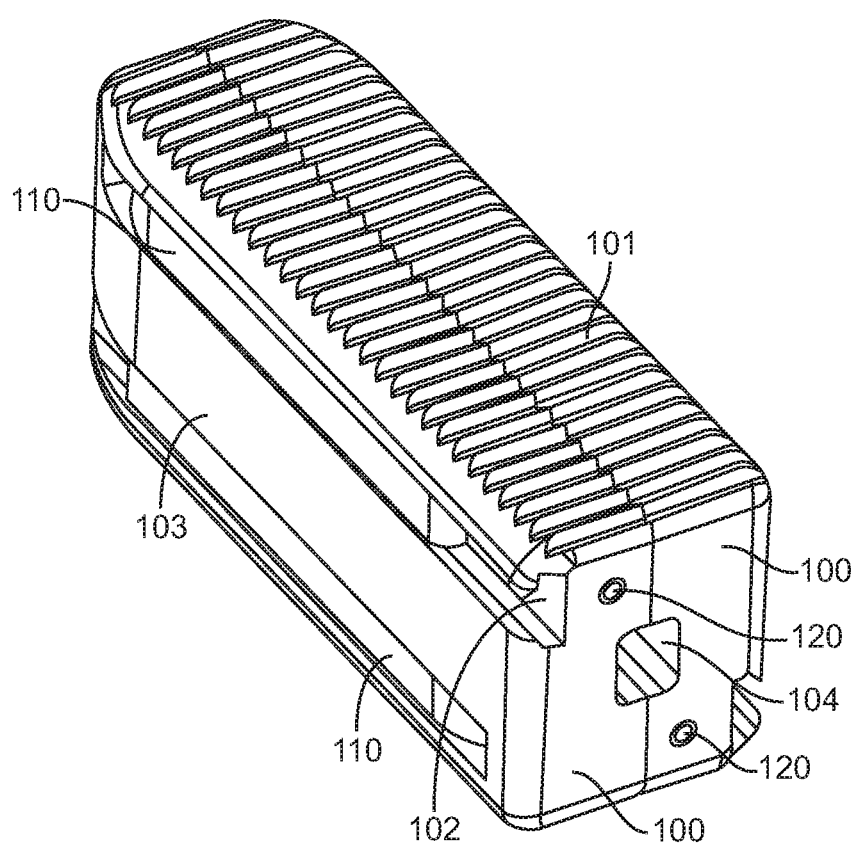
FIG. 11 illustrates a perspective view of still another exemplary embodiment of an interbody fusion device in the collapsed configuration.

FIG. 11 shows an additional embodiment where the elongated members 100 have top and bottom surfaces 101 with a plurality of anti-migration teeth, smooth side walls 103, and instrument engagement features 104. In this embodiment of the interbody, the spanning components 110 consist of four ratcheting members. In the collapsed state the spanning components 110 are positioned in dovetailed slots 102 along the smooth side walls 103 in the elongated members 100. The slots 102 and the spanning components 110 have corresponding dovetail profiles to retain the spanning members 110 in their corresponding slot 102. The spanning members 110 are attached to the elongated members 100 via a series of pins 120 that traverse through both the elongated members 100 and the spanning components 110.

Figure 12:
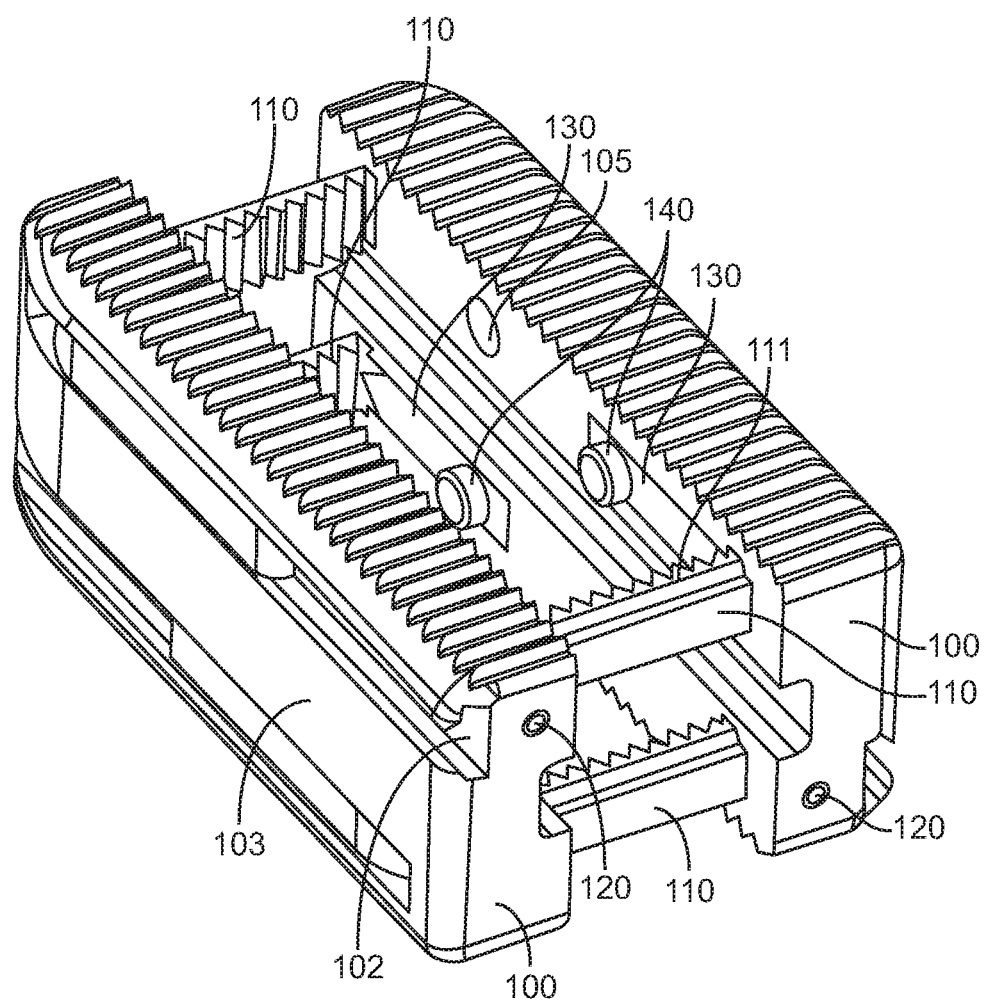
FIG. 12 illustrates a perspective view of the embodiment of FIG. 11 in the expanded configuration.

FIG. 12 shows the implant of FIG. 11 in its expanded state. The ratchet teeth 111 on the spanning components 110 engage with the lock component 130 to fix the implant in its expanded position. The lock components 130 are attached to the elongated members 100 via the lock fixation pins 140 with the heads of the lock fixation pins being set in a recess 105 in the elongated members 100 when in the collapsed state. In order for the spanning components 110 to move from their position in the collapsed state into their position in the expanded state they will need to elastically deform during the time when they transition from being in the slots 102 in the elongated members 100 to being perpendicular to the smooth side walls 103 and spanning between the elongated members 100.

Figure 13:
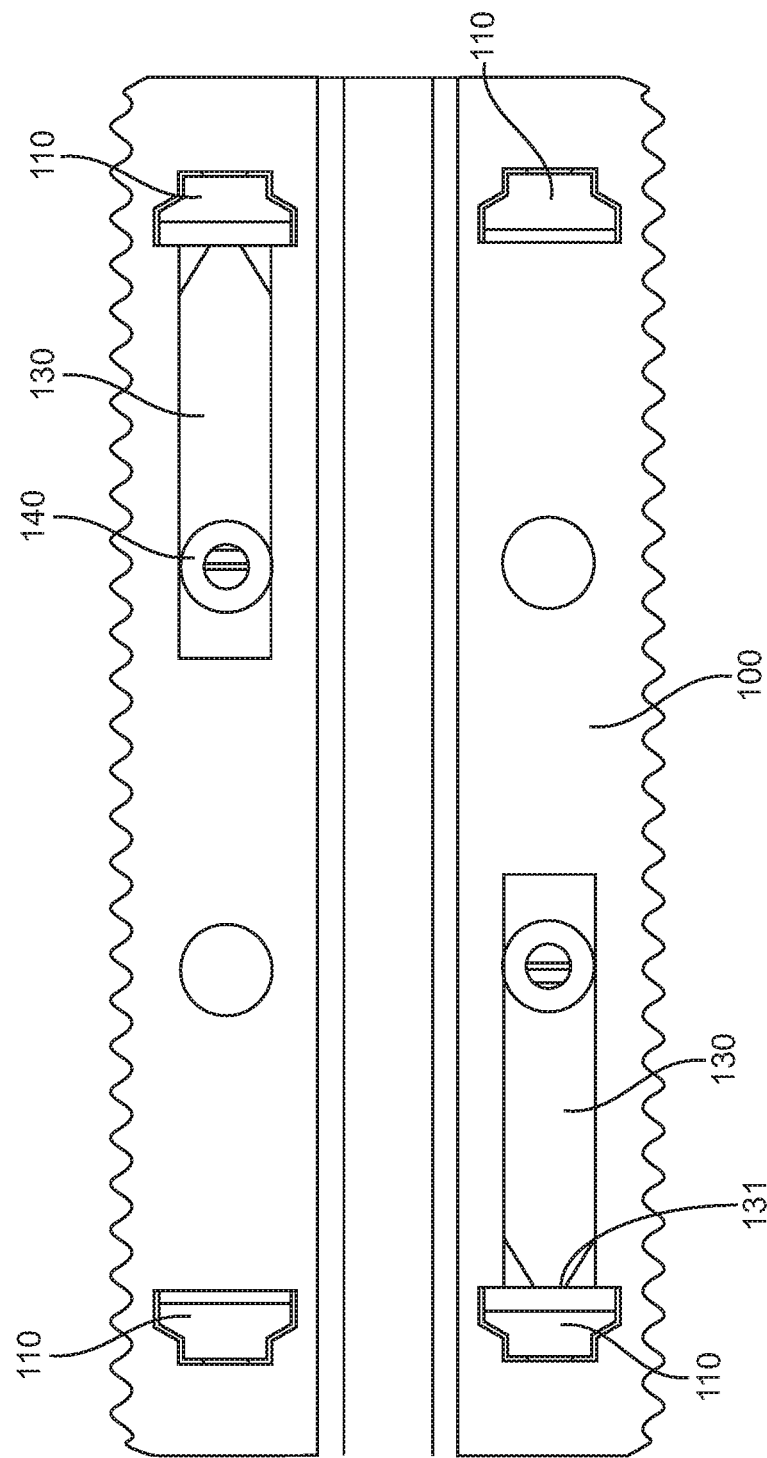
FIG. 13 illustrates a partial cross-section of the embodiment in FIG. 11.

FIG. 13 shows a cross section of the implant in FIG. 11 at the medial wall of the elongated member 100. Visible in this cross section are the spanning components 110, the lock 130, and the lock fixation pins 140. Also visible are the interaction between the locks 130 and the spanning members 110 at junction 131 where the lock ratchets along the ratchet teeth 111 in the spanning components 110.

Figure 20A:
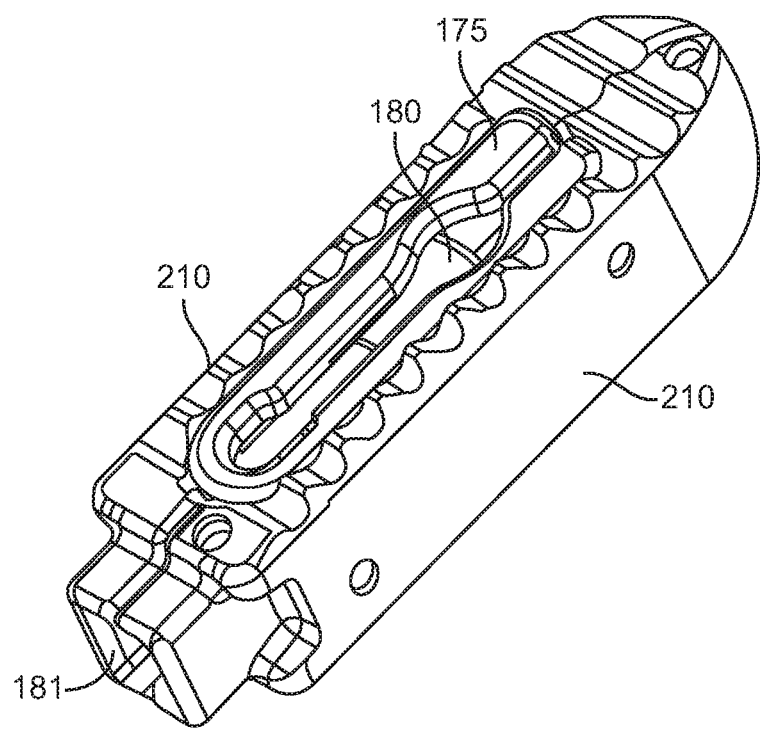
FIGS. 20A-20E illustrate perspective or partial cross-sectional views of other features of exemplary embodiments of the interbody fusion device.

FIGS. 20A-20E illustrate various features of other exemplary embodiments. FIG. 20A is a perspective view of an exemplary embodiment of the interbody fusion device (also referred to as the implant) in the collapsed configuration. The implant includes two elongated members 210 that are attached with two spanning members 175 stacked on top of one another. The elongated members 210 include a relief cut 180 that is sized to receive the spanning components and alleviates loading of spanning components 175. Receptacle 181 is formed when the two elongate members are in the collapsed configuration and allow a surgical instrument to be coupled thereto, as will be discussed elsewhere in this specification.

Figure 20B:
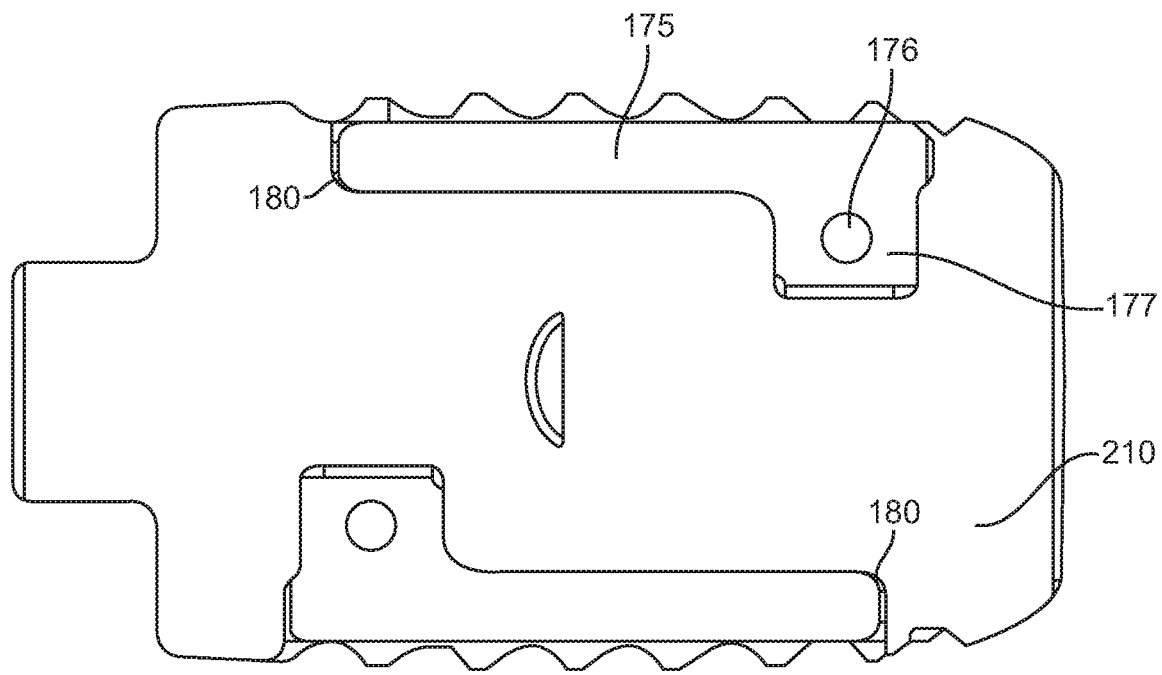

FIG. 20B illustrates a cross-section of FIG. 20A taken through elongated member 210. This view illustrates how the spanning member 175 is coupled to the elongate member 210. The posts 177 on the spanning members 175 and cross pins 176 are designed to attach the spanning components 175 to the elongated members 210. The spanning member is seated in recess 180.

Figure 20C:
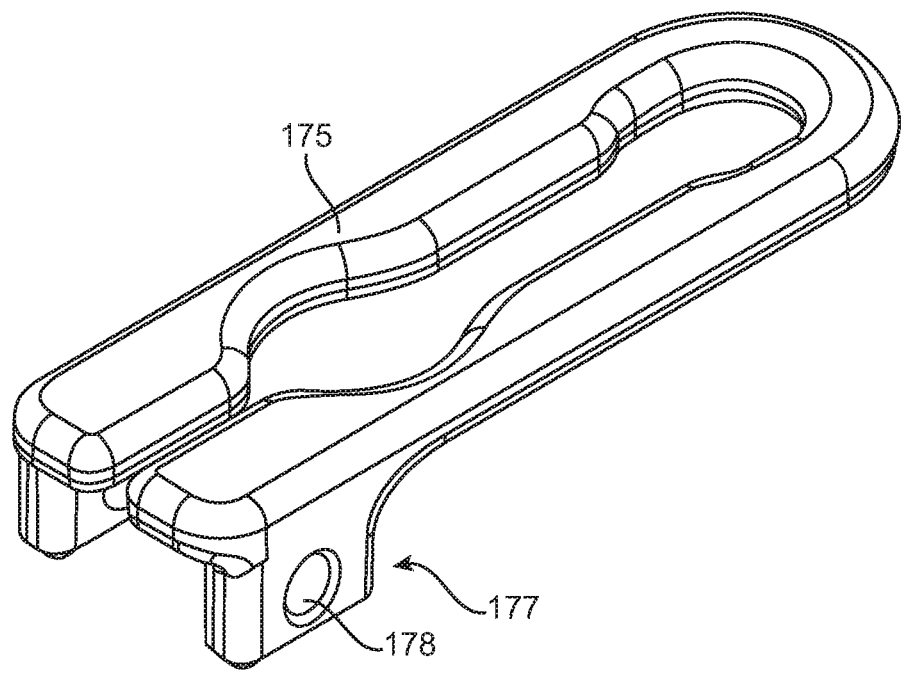

FIG. 20C is a perspective view illustrating the spanning member 175 more clearly. The spanning component 175 consists of two engagement posts 177 and two holes 178 to engage with pins 176. The spanning component is formed from two arms coupled together with a hinge that allows the arms to open or close. A relief cut in both arms allows the free end of the arms to pivot inwardly or outwardly thereby permitting the elongate members to remain substantially parallel with one another as they open up outward.

Figure 20D:
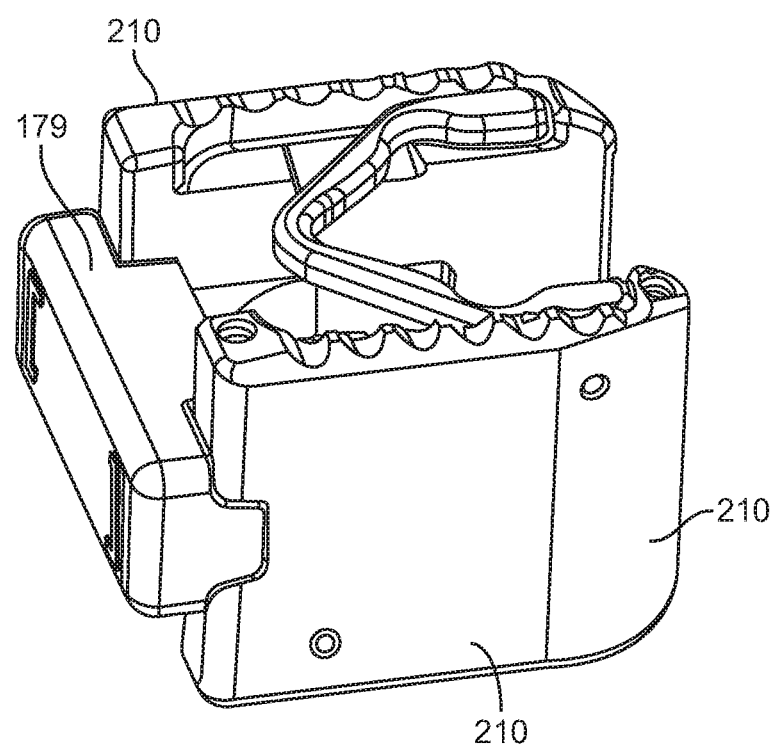
Figure 20E:
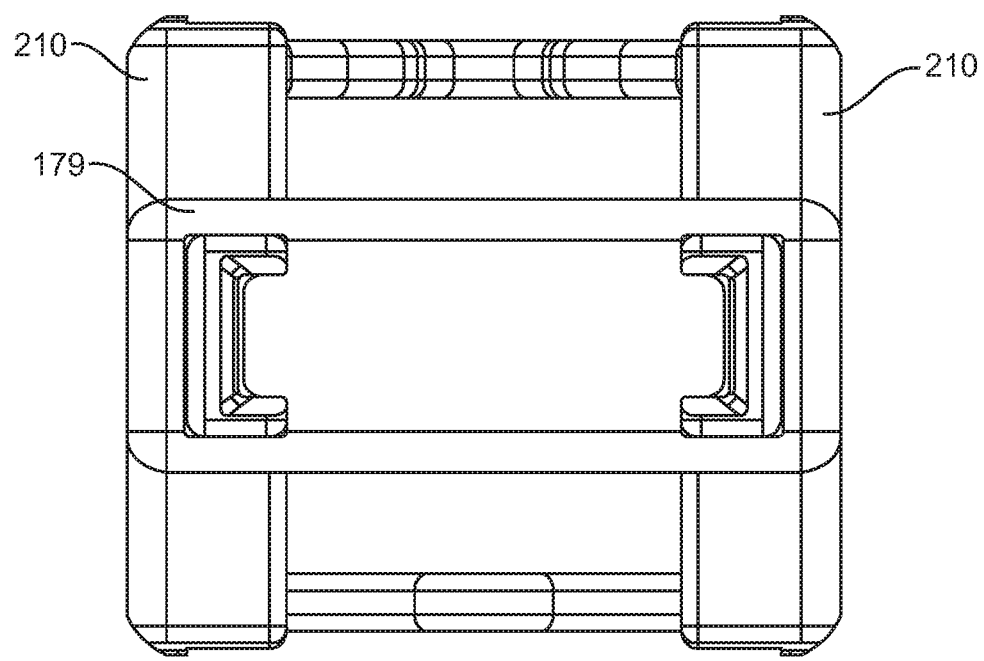

FIG. 20D illustrates the interbody fusion device in the expanded or distracted configuration with the spanning component also in the expanded configuration. An optional posterior cap 179 may be coupled to the elongated members 210 in order to lock the implant into the expanded configuration. A surgeon may use forceps or another surgical instrument to engage the posterior cap with the elongate members. The posterior cap may have a snap fit, press fit, or other coupling mechanism for attachment to the elongate members. In addition to locking the implant in the expanded configuration, the posterior cap also adds stability to the implant and also aids in containment of bone grafting material. FIG. 20E is a rear view of the implant in FIG. 20D and highlights the posterior cap 179.

Figure 21A:
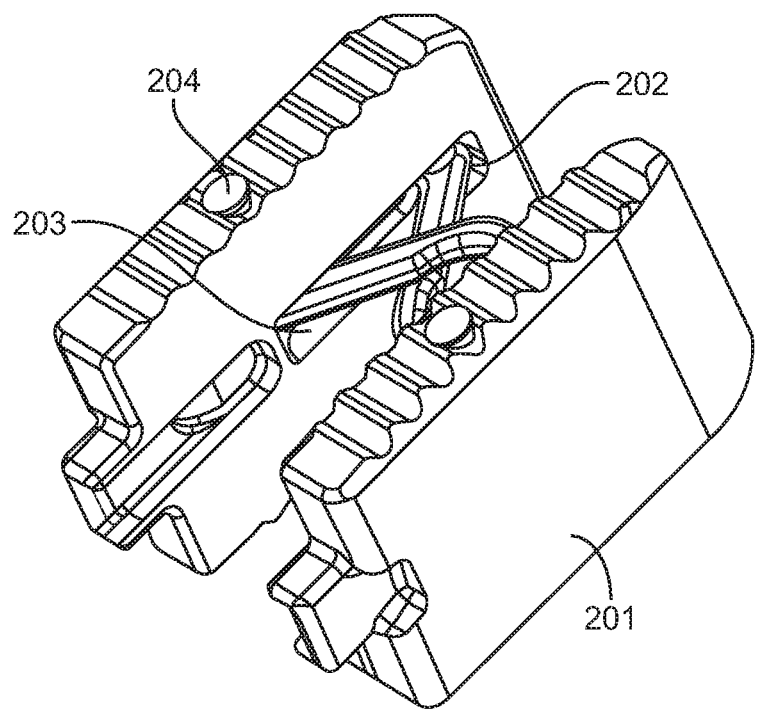

FIGS. 21A-21G illustrate various aspects of other exemplary embodiments of the implant. FIG. 21A is a perspective view of an interbody fusion device in the expanded configuration. The implant has two elongated members 201 that are attached with two spanning members 202. Spanning members 202 are disposed in a recessed pocket 203 that is formed in the center of the elongated members 201 when they are in their collapsed state. Spanning members 202 are attached to elongated members 201 via cross pins 204.

Figure 21B:
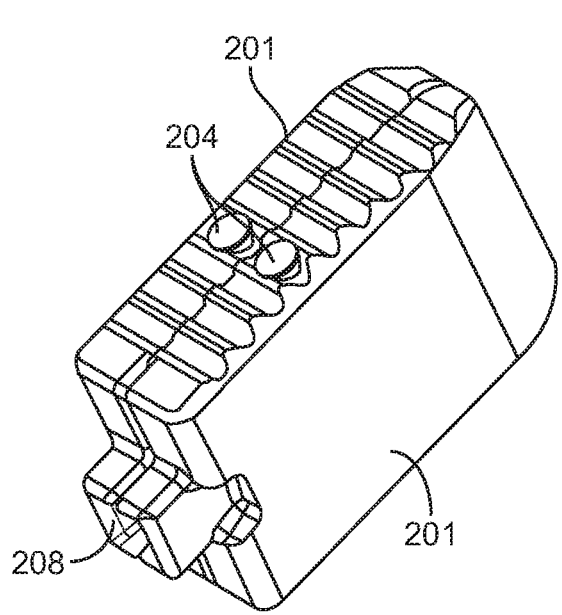

FIG. 21B illustrates the interbody fusion device of FIG. 21A in the collapsed configuration. Receptacle 208 is formed when the elongate members 201 are collapsed. Receptacle 208 allows the implant to be coupled to other surgical instruments as will be discussed elsewhere.

Figure 21C:
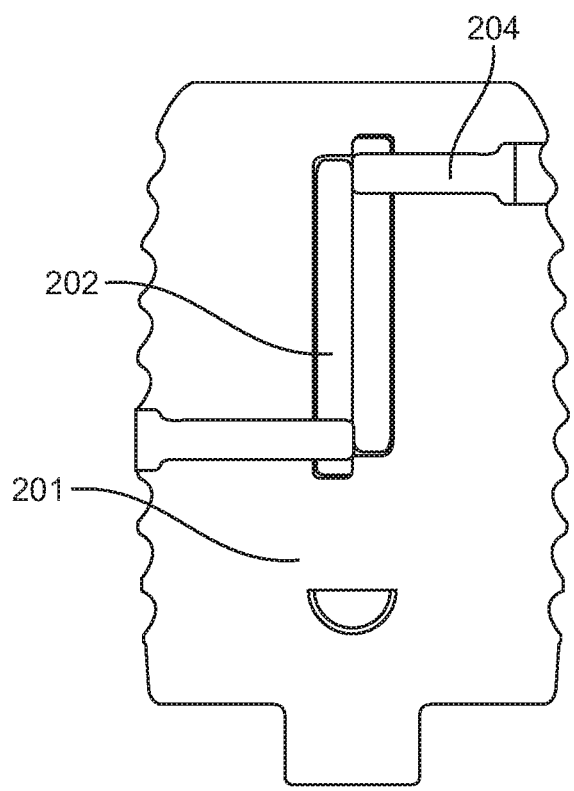

FIG. 21C illustrates a cross-section of the embodiment in FIG. 21A. The cross-section is taken through elongated member 201. This view highlights the engagement between elongated member 201, cross pins 204 and spanning components 202.

Figure 21D:
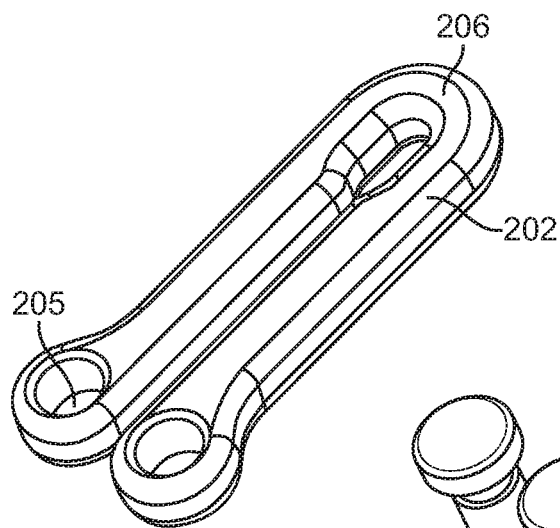

FIG. 21D illustrates a spanning component from the embodiment of FIG. 21A. Two holes 205 are designed to fit cross pins 204 to attach to the implant. In this embodiment, the spanning members are designed to deform at deformation zone 206 and pivot around cross pins 204 during width expansion. The cross member (also referred to as a spanning member) includes two arms coupled together with a hinge. The free end of each arm includes the hole 205 for receiving a pin.

Figure 21E:
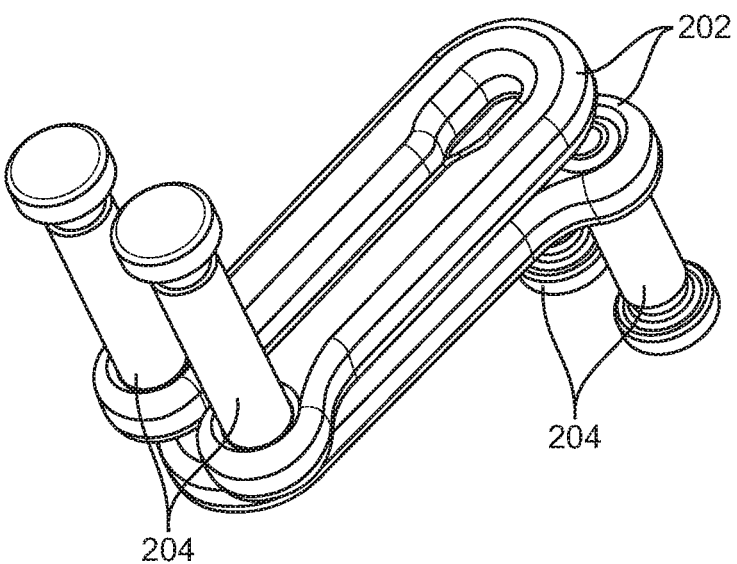

FIG. 21E illustrates the orientation of the two spanning members 202 relative to one another in the embodiment of FIG. 21A. In this embodiment, the upper spanning member has an open end and a closed end facing in a first direction. The lower spanning member has an open end and a closed end facing in a second direction opposite the first direction. Pins 204 are also show in the holes of each spanning member.

FIG. 21F illustrates an alternative embodiment of the interbody fusion device of FIG. 21A. In the embodiment of FIG. 21A, the holes in the elongate member and the pins for each spanning member are disposed on the same side of the elongate member. In FIG. 21F, one hole is on a superior surface of the implant and the second hole is on the inferior surface of the implant. Thus the corresponding pins also are pressed in from opposite sides of the implant. One is pressed in from the superior surface and the other from the inferior surface. Similarly, the second spanning member has one pin pressed in from each side of the elongate member.

FIG. 21G illustrates a top view of the embodiment in FIG. 21F with the stagger pin configuration.

FIGS. 22A-22D illustrate aspects of another exemplary embodiment of an interbody fusion device. FIG. 22A illustrates a perspective view of the implant in the collapsed configuration. Here, the elongated members 209 are attached with only one spanning member 202. Spanning member 202 fits into a recessed pocket 203 that is formed in the center of each of the elongated members 209 when they are in their collapsed state. Spanning member 202 is attached to the elongated members 201 via cross pins 204.

FIG. 22B illustrates a top view of the interbody fusion device in FIG. 22A. FIG. 22C shows a cross-section of the elongate member 201, showing the engagement between elongated member 209, cross pins 204 and spanning member 202.

FIG. 22D illustrates the spanning member 202 which includes two arms connected together with a hinge. The free ends of the arms include holes for receiving the pins 204.

Figure 23C:
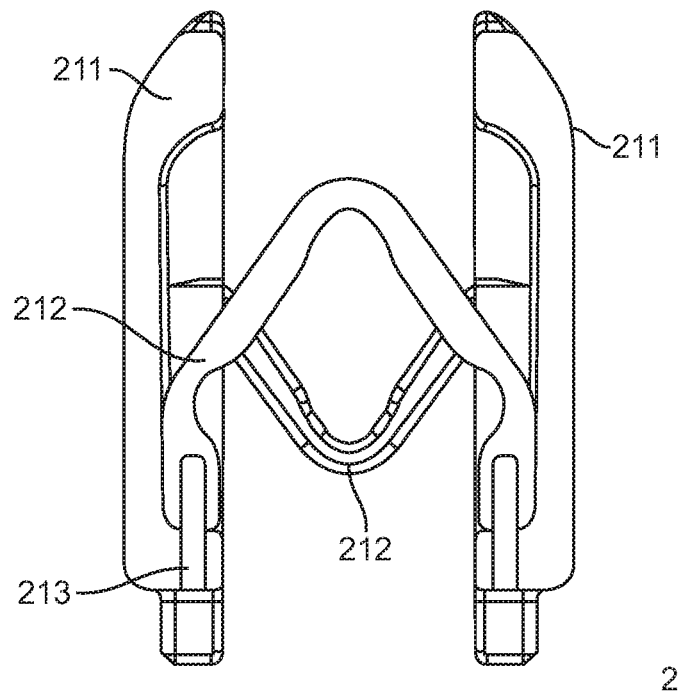

FIGS. 23A-23E illustrate features of another exemplary embodiment of an interbody fusion device. FIG. 23A illustrates a perspective view of the interbody fusion device in the collapsed configuration. In this embodiment, the elongated members 211 are coupled together with two spanning members 212. A receptacle 214 allows the implant to be engaged with a surgical instrument for delivery, as will be discussed elsewhere in this specification. The superior and inferior surfaces of the implant optionally have anti-movement teeth, and this feature may optionally be included in any of the embodiments of implants disclosed herein.

FIG. 23B illustrates the implant of FIG. 23A in the expanded configuration. FIG. 23C shows a cross-section of the implant in FIG. 23A in the expanded configuration. The cross-section is taken through spanning component 212. Cross pins 213 attach spanning components 212 to elongated members 211 and allow pivotal motion about the longitudinal axis of elongated members 211.

Figure 23D:
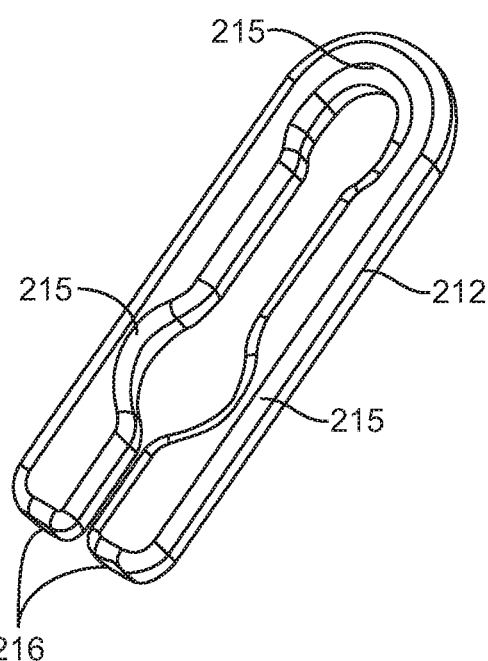

FIG. 23D illustrates the spanning member 212 in more detail. The spanning member 212 includes two arms connected together with a hinge. The free ends of the arms each have holes 216 for receiving cross pins 213 for securing the spanning member 212 to the elongate member. In addition the main hinge, each arm has an arcuate cutout region which forms a secondary hinge 215. The secondary hinge allows the arm to further bend independently of the main hinge, such as in the case when the elongate members expand outward, they can remain in a substantially parallel configuration.

Figure 23E:
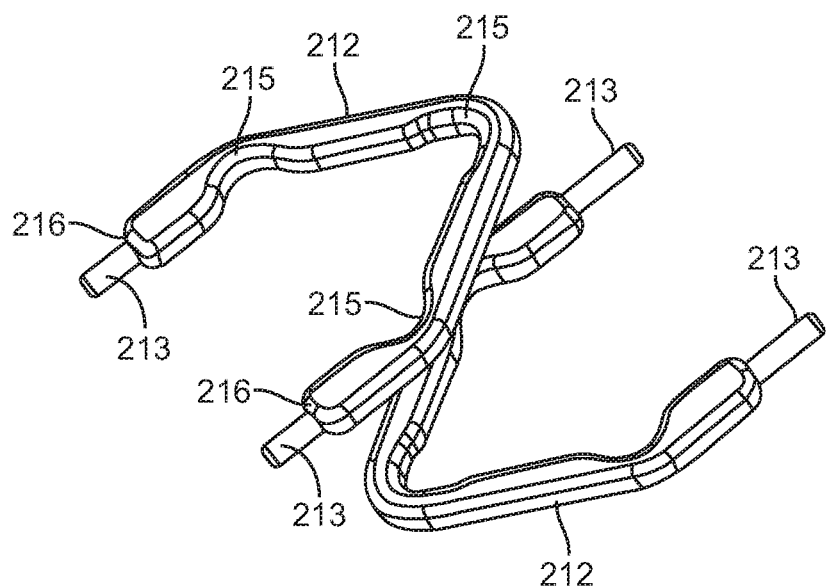

FIG. 23E illustrates both spanning members stacked on top of one another as they would be in the implant of FIG. 23A with the cross-pins inserted in holes 216. A portion of both arms in each spanning member forms an angle with the main hinge, and the secondary hinge allows the free end of the arm to bend inward toward the opposite free end of an arm, thereby permitting the free ends of both arms to remain substantially parallel to one another. This allows the elongate members to also remain substantially parallel to one another in the expanded configuration.

Implantation.

Figure 14:
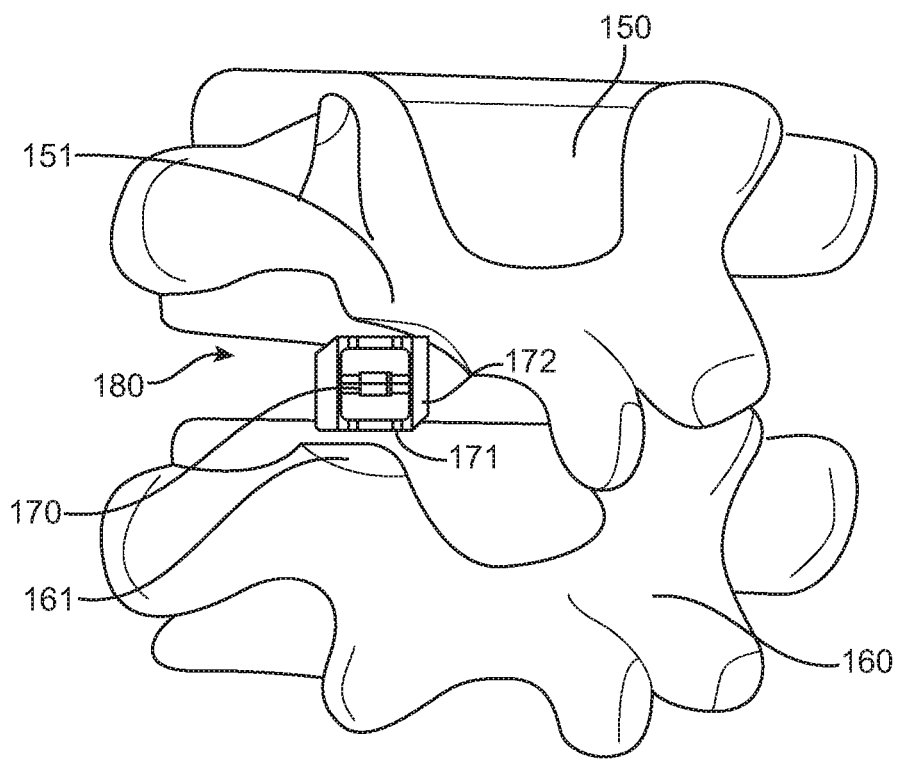
FIG. 14 illustrates a side view of an interbody fusion device disposed in the intervertebral disc space.

FIG. 14 show a superior vertebral body 150, an inferior vertebral body 160, and the intervertebral space 180 between them. The superior articular process 161 of the inferior vertebral body 160 and the inferior articular process 151 of the superior vertebral body 150 have been removed on one side to allow for access into the intervertebral space as is common in a transforaminal interbody fusion procedure (TLIF). FIG. 14 shows the implant 170 being inserted in to the intervertebral space 180 with the smooth side walls contacting the endplates of the vertebral bodies 150 and 160. The implant 170 may be any of the embodiments of implants disclosed herein.

Figure 15:
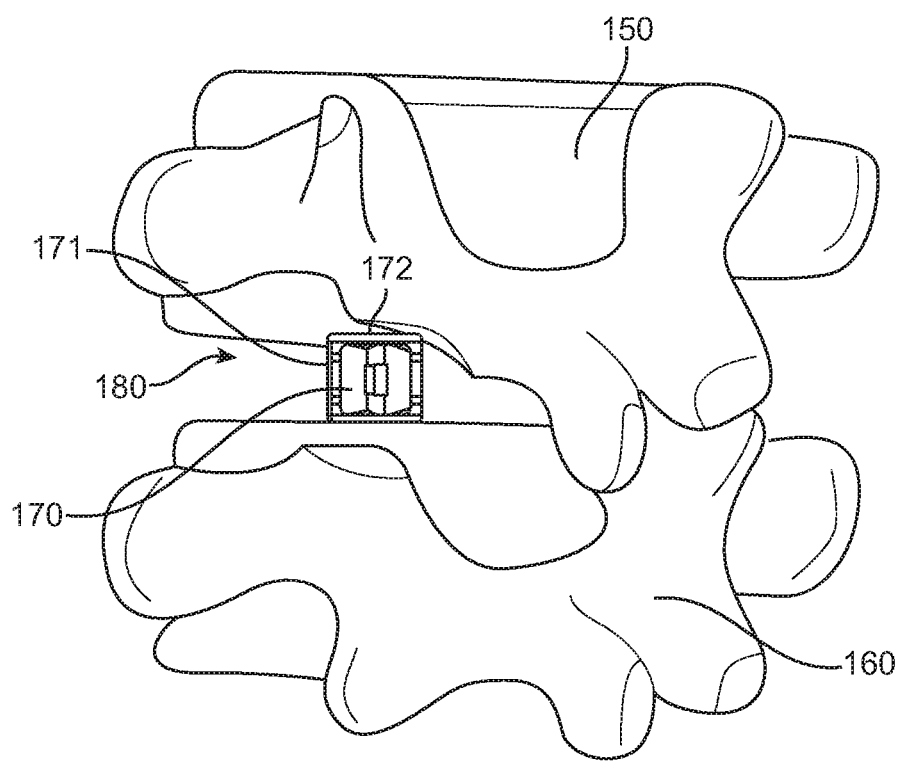
FIG. 15 illustrates a side view of the interbody fusion device in FIG. 14 rotated 90 degrees.

FIG. 15 shows the implant rotated 90 degrees so that the top and bottom surfaces of the implant 172 are contacting the endplates of the vertebral bodies. Due to the difference in the height of the implant relative to the width of the implant this rotation results in the distraction of the vertebral bodies 150 and 160.

Figure 16:
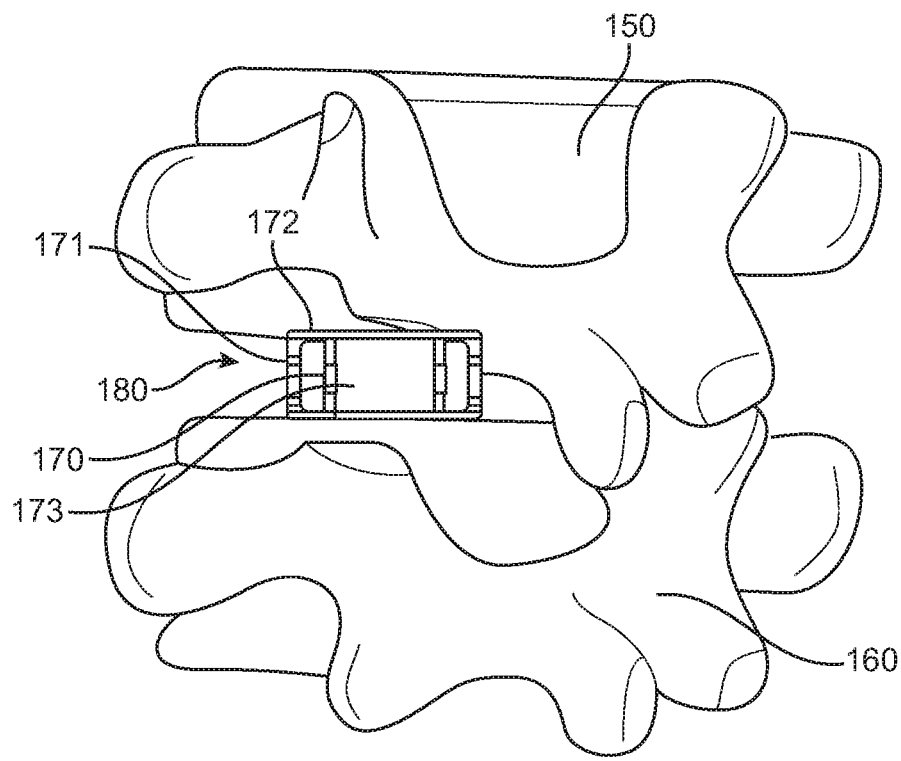
FIG. 16 illustrates a side view of the interbody fusion device in FIG. 15 in the expanded configuration.

FIG. 16 shows the implant 170 in an expanded state creating a wider and more stable footprint for the implant and ample room for the insertion of graft material into the space created in the implant 173. The implant in this exemplary method of implantation may be any of those described herein.

Figure 17:
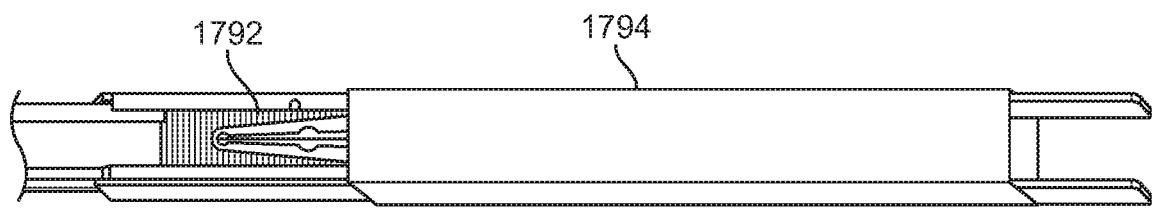
FIG. 17 illustrates a perspective view an interbody implant coupled to an insertion guide device.

FIGS. 18A-18F illustrate an exemplary method of delivering an interbody implant using an insertion guide device such as the one illustrated in FIG. 17.

Figure 18A:
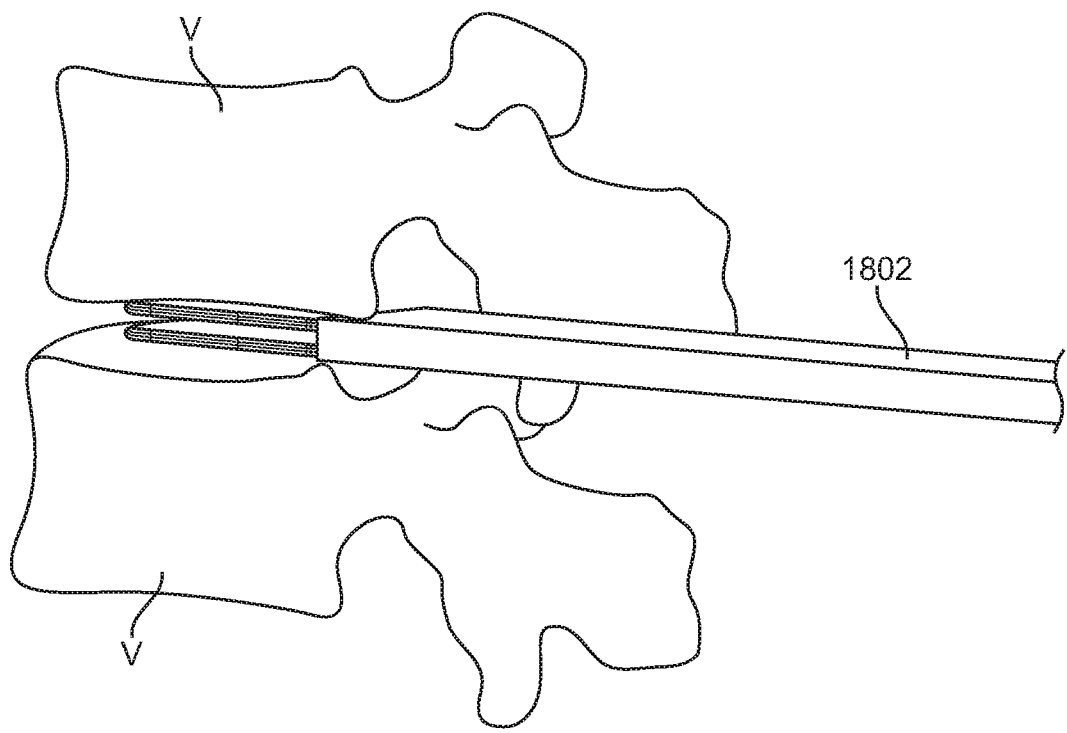
FIGS. 18A-18F illustrate a side view of insertion of the insertion guide device into the intervertebral disc space and delivery of an interbody implant.
Figure 18B:
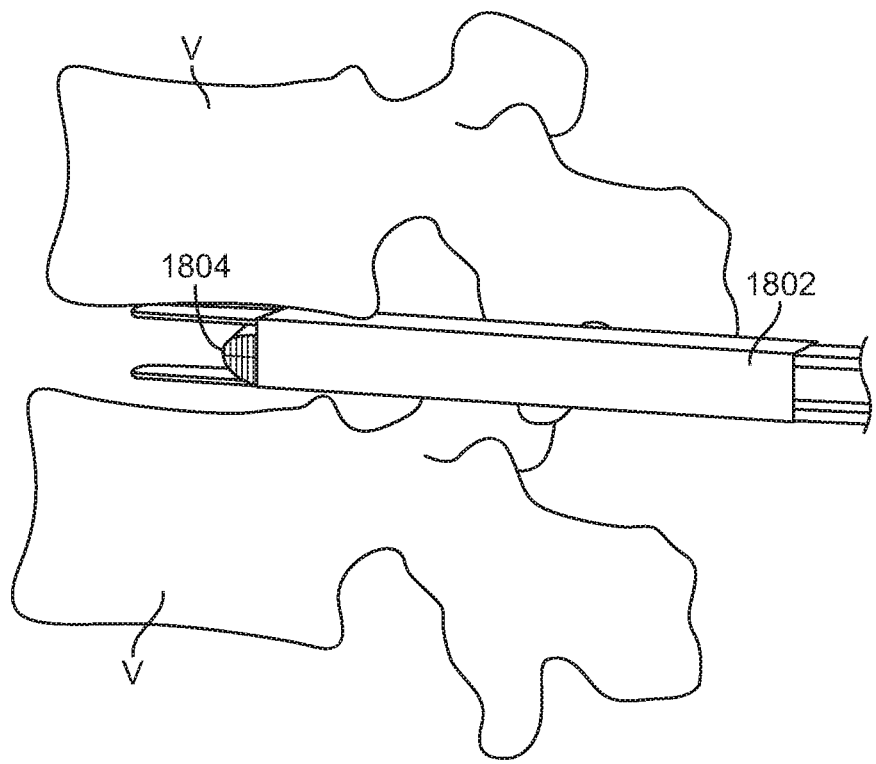
Figure 18C:
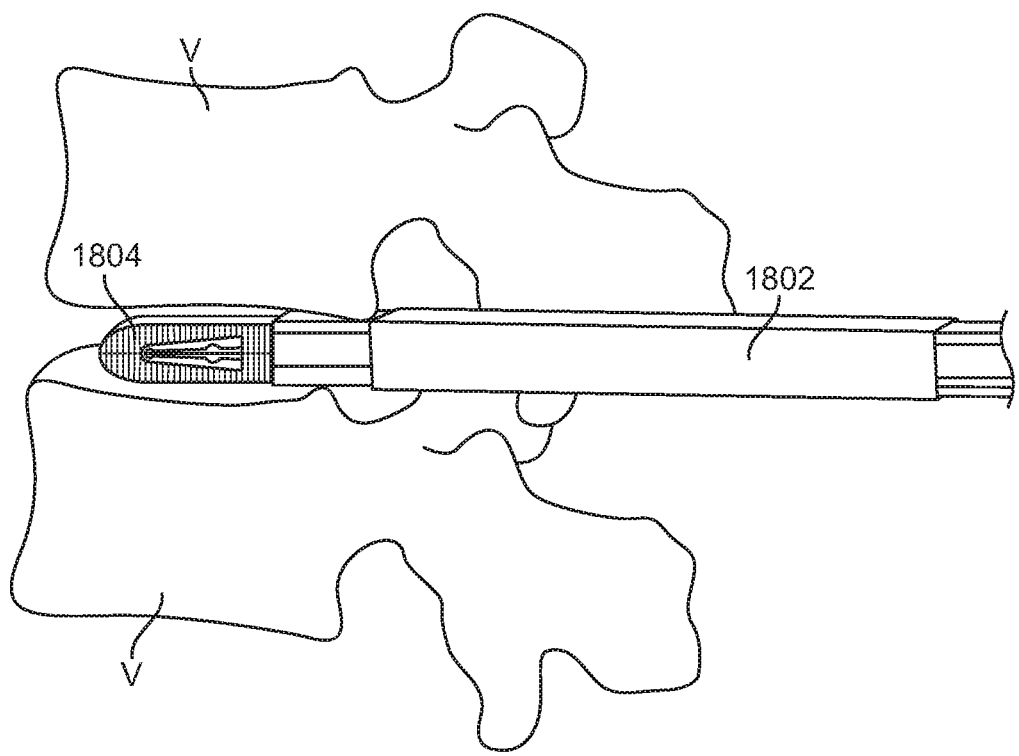
Figure 18D:
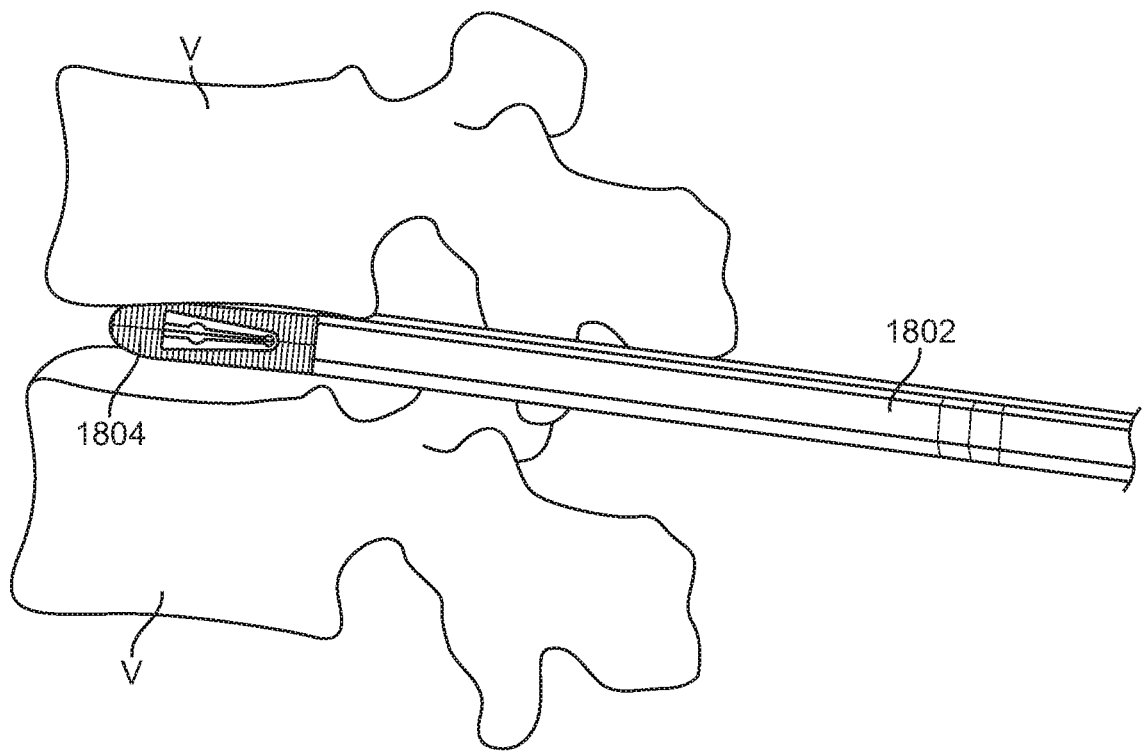

In FIG. 18A, the insertion guide device 1802 is inserted into the intervertebral disc space between adjacent vertebrae V. In FIG. 18B, the interbody implant 1804 is advanced distally out of the insertion guide device 1802 until it is exposed from the expandable portion of the insertion guide device and positioned in a desired location between the vertebrae, as illustrated in FIG. 18C. The anti-migration teeth of the upper and lower surfaces of the implant face laterally and medially outward and the smooth lateral surfaces face upward and downward and engage the vertebral end plates. FIG. 18D is similar to FIG. 18C but illustrates a longer portion of the insertion guide device.

Figure 18E:
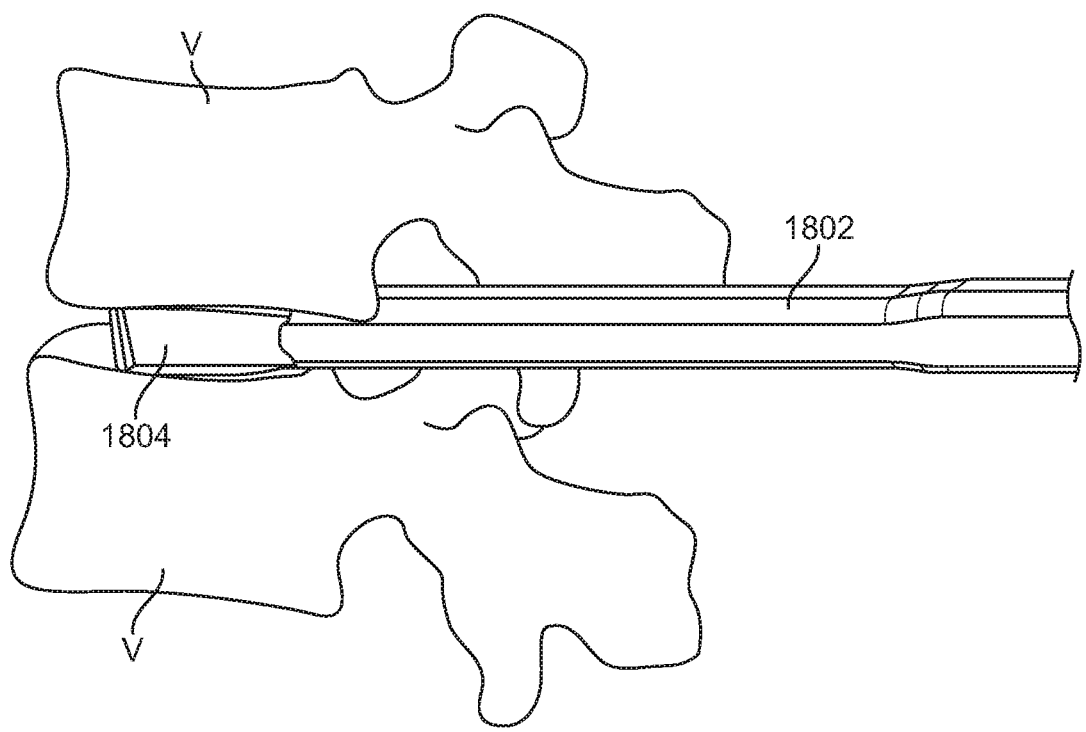
Figure 18F:
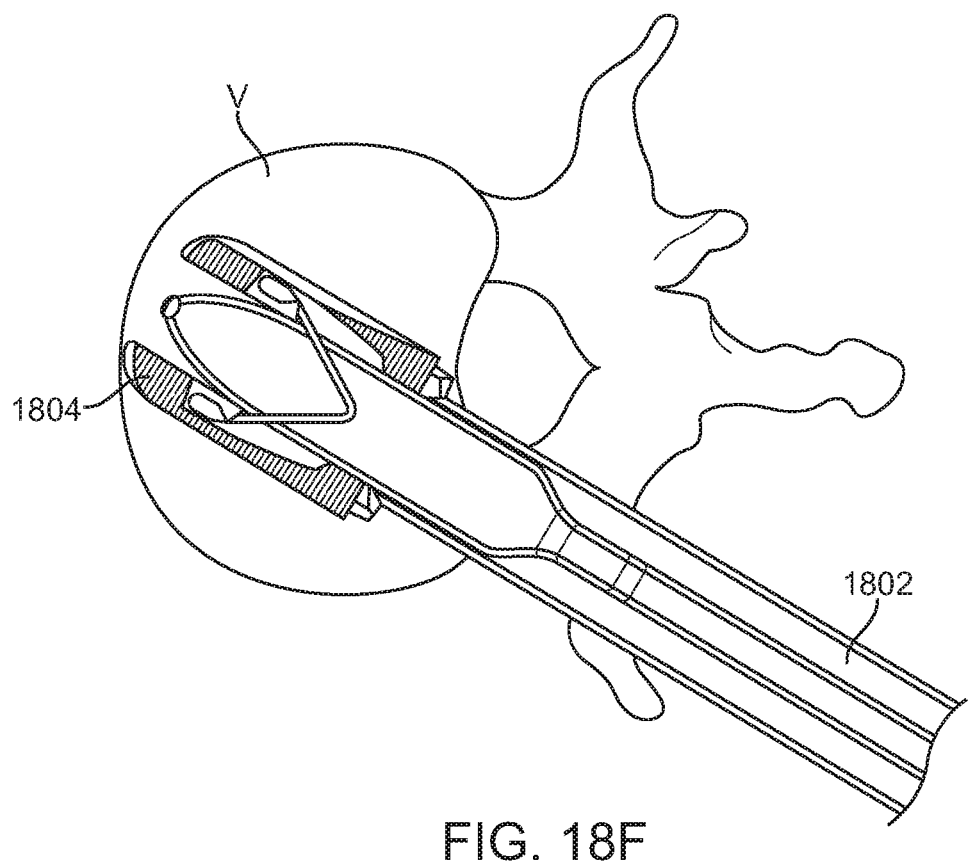

In FIG. 18E, the interbody implant and the insertion guide device have been rotated 90 degrees so that the textured surfaces of the interbody implant are in engagement with the endplates of the vertebrae and the smooth lateral surfaces of the implant now face laterally and medially outward. FIG. 18F is a top view of the interbody implant and insertion guide device with the upper vertebra removed for ease in viewing. Additionally, the interbody implant has been laterally expanded to increase its width. The implant and the insertion guide device may be any of the embodiments disclosed herein.

Figure 27A:
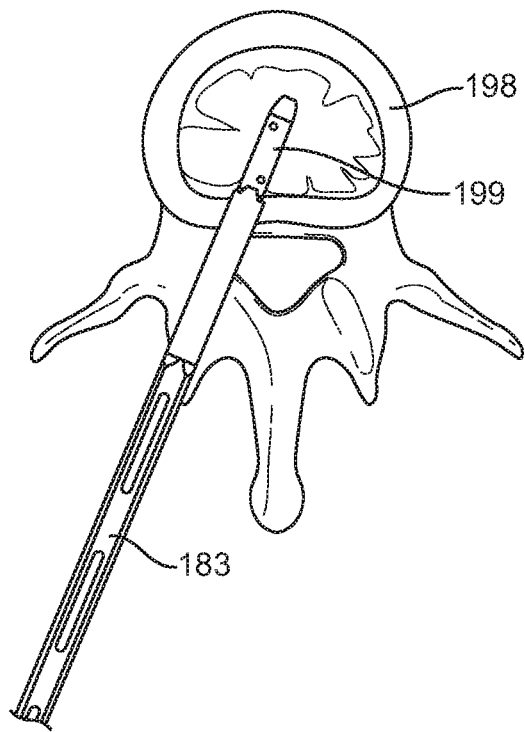
FIGS. 27A-27C illustrate a top view of implantation of an interbody fusion device.
Figure 27B:
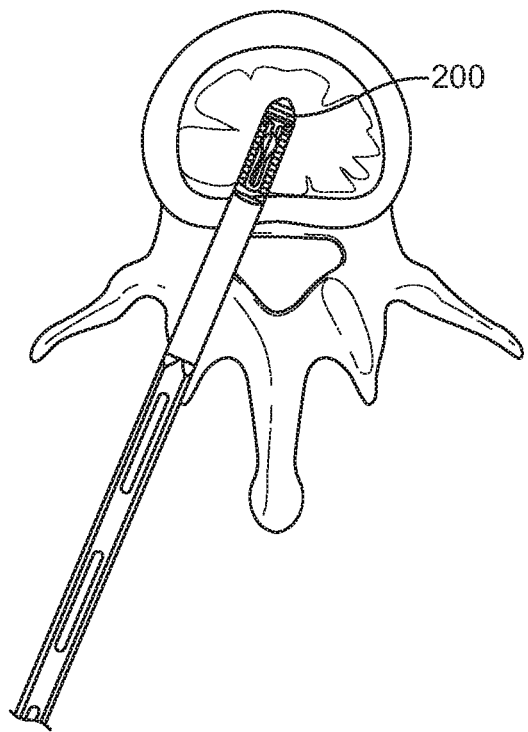
Figure 27C:
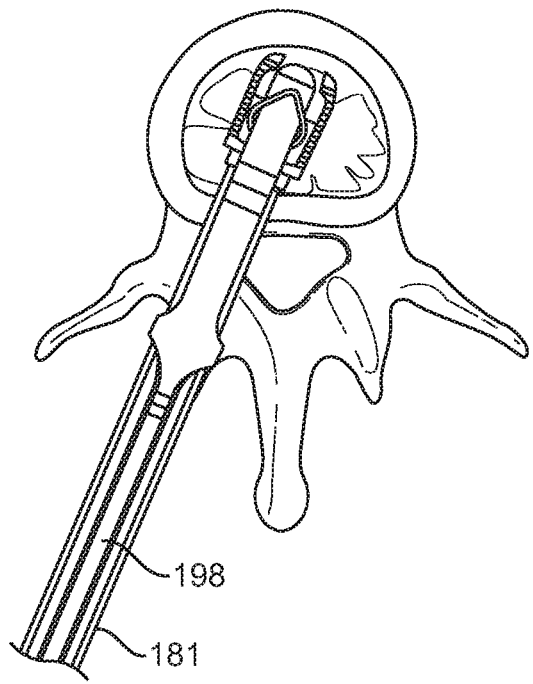

FIGS. 27A-27C illustrate other aspects of implant delivery and deployment. FIG. 27A shows a top view of an implant engaged with an insertion instrument 183 on an inferior vertebral body 198. The superior vertebrae has been omitted from the figure for convenience. The implant has been inserted into the intervertebral disc space with the smooth side walls 199 contacting the endplates. The insertion tool may be used to deliver the implant, or the insertion tool may be used in conjunction with the insertion guide previously described above.

FIG. 27B shows the implant rotated 90 degrees so that the top and bottom surfaces 200 of the implant are contacting the endplates of the vertebral bodies. The top and bottom surfaces preferably have anti-migration teeth to prevent unwanted movement. Rotation is accomplished by rotating the insertion tool.

FIG. 27C shows the interbody fusion device disengaged from the insertion tool and now engaged with the expansion instrument. The expansion instrument has been advanced distally thereby expanding the implant into the expanded configuration. The expansion instrument 187 and shims 181 are still coupled to the implant. After proper positioning and expansion have been confirmed, the expansion instrument and the shims may be removed.

Surgical Instruments.

FIG. 17 illustrates an interbody implant 1792 coupled to the insertion guide device 1794. The interbody implant is in its collapsed configuration, and it may be any of the embodiments disclosed herein. The insertion guide device may be any of the embodiments disclosed in this specification, or disclosed in U.S. patent application Ser. No. 14/322,589 filed Jul. 2, 2014, and previously incorporated herein by reference. The insertion guide device preferably includes a pair of elongate insertion plates with a resilient member disposed thereover. The implant is passed through a channel formed by the elongate insertion plates, the resilient member expands to accommodate the implant.

Figure 19A:
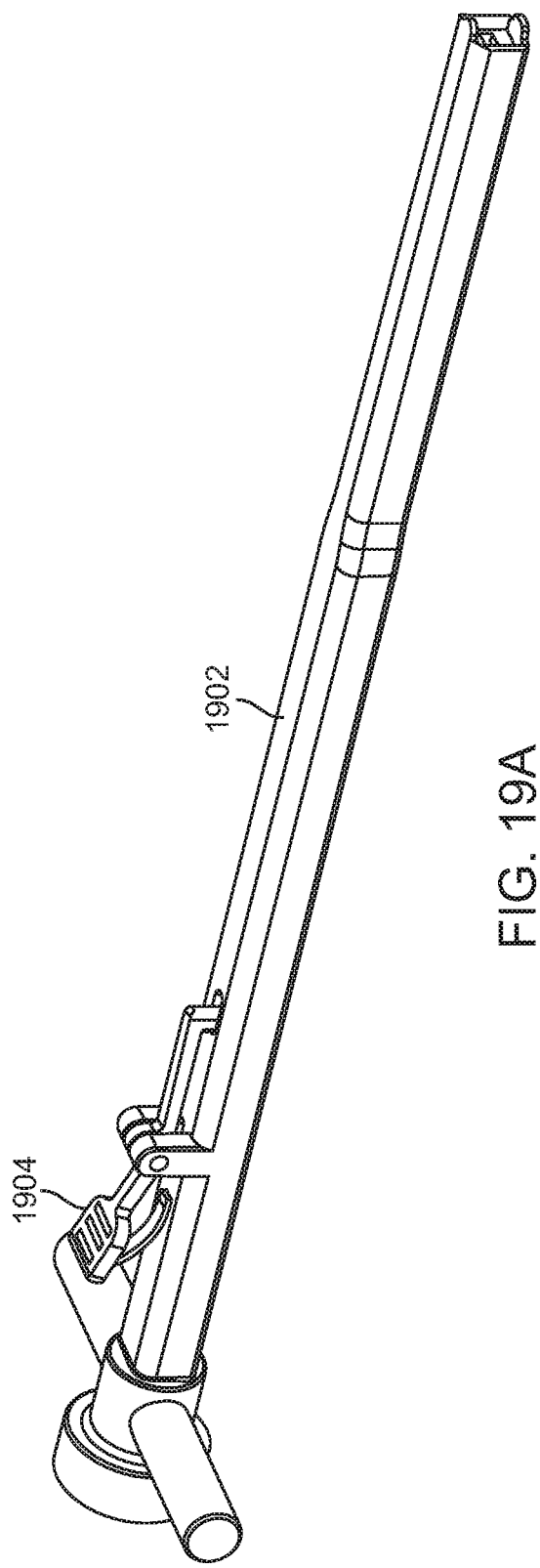
FIGS. 19A-19B illustrate a perspective view of a pusher element for pushing an interbody implant from the insertion guide device.
Figure 19B:
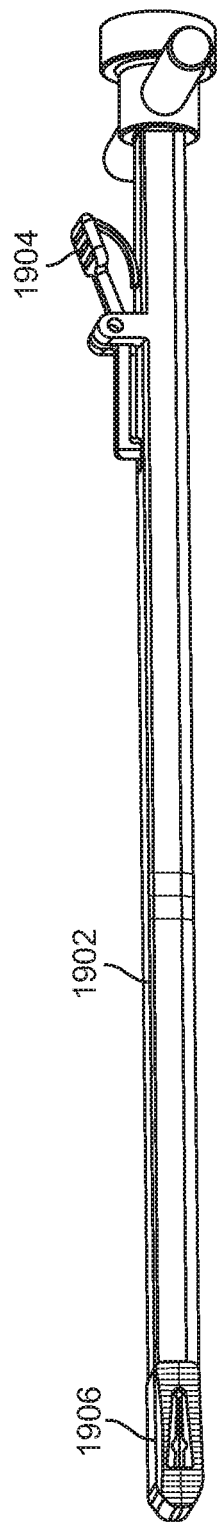

FIGS. 19A-19B illustrate the pusher element which may be advanced or retracted by an operator to move the interbody implant through the insertion guide device previously described. In FIG. 19A, the pusher element 1902 includes an elongate shaft with a handle on the proximal end for ease in manipulation. A lever 1904 helps lock the pusher to the interbody implant. FIG. 19B illustrates the interbody implant 1906 coupled to the pusher element 1902. A leaf spring is disposed under the actuation lever thereby biasing the lever in the up position so that the pusher remains locked with the interbody implant. When the lever is moved, the implant may be decoupled from the pusher.

Figure 24A:
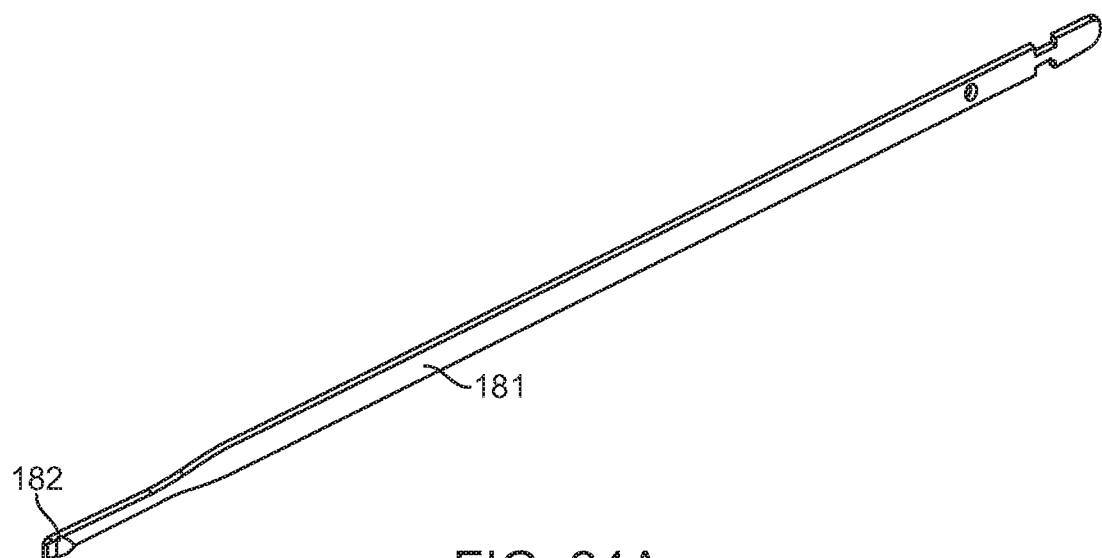
FIGS. 24A-24C illustrate perspective or partial cross-sectional views of engagement of an interbody fusion device with a shim used to advance the implant with an insertion instrument.
Figure 24B:
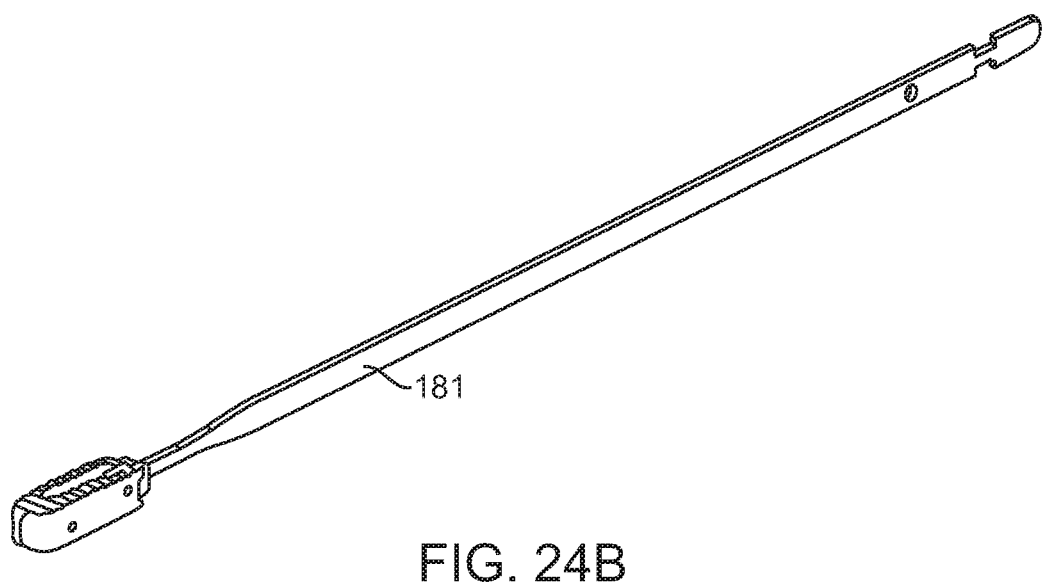
Figure 24C:
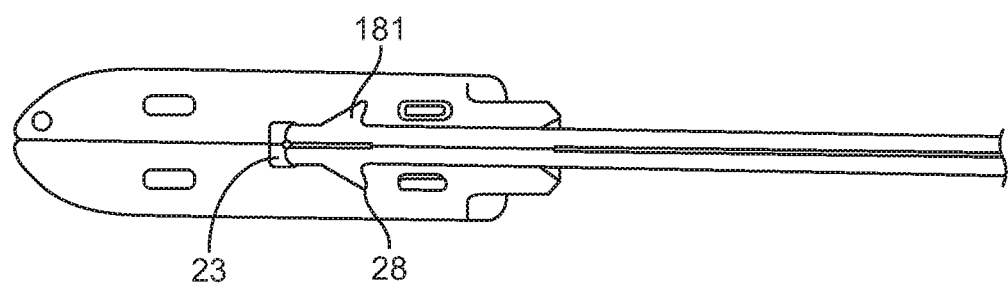

FIGS. 24A-24C illustrate engagement of the interbody fusion device with a shim used to advance the implant along an insertion instrument. FIG. 24A illustrates a perspective view of a shim used to engage any of the interbody fusion devices described herein. The shim 181 includes an elongate shaft having a mating feature 182 on a distal portion of the elongate shaft and that is configured to engage with any interbody fusion device, such as notch 28 as seen in FIG. 2, or any of the receptacles described herein, such as receptacle 214 in FIG. 23A. The proximal end of the shim includes notches for engagement with an insertion tool.

FIG. 24B shows engagement of the shim 181 with any interbody fusion device disclosed herein. The mating feature 182 on the shim is releasably coupled with the corresponding notch, receptacle, or other mating feature on the implant.

FIG. 24C illustrates a cross-section in greater detail showing engagement of the shim 181 mating feature 182 with the implant. Here two shims 181 are illustrated. Shims 181 fit in slot 23 of the implant and engage with the implant in notch 28. The mating feature of the shim in this embodiment includes an enlarged head having an angled protrusion that is configured to be advanced forward into the implant and into the corresponding receptacle, but cannot easily be pulled out when the implant is in the collapsed configuration because the receptacle has a flat shoulder which engages the flat portion of the angled protrusion and prevents it from pulling out.

Figure 25A:
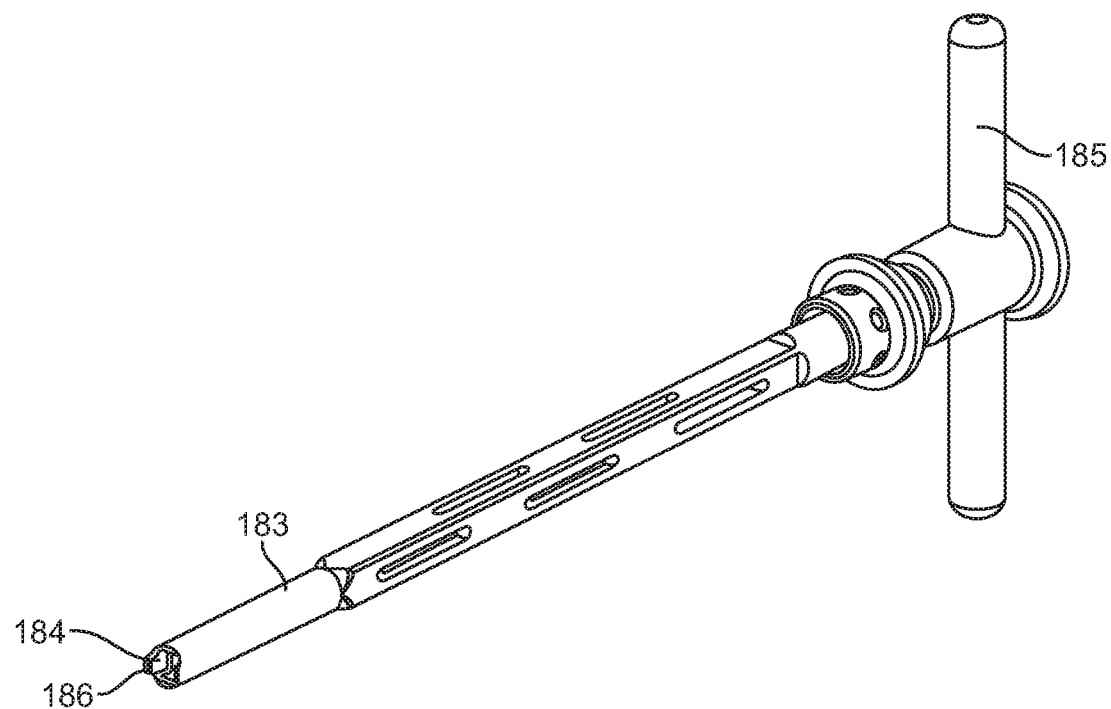
FIGS. 25A-25B illustrate a perspective view of an exemplary embodiment of an insertion tool.
Figure 25B:
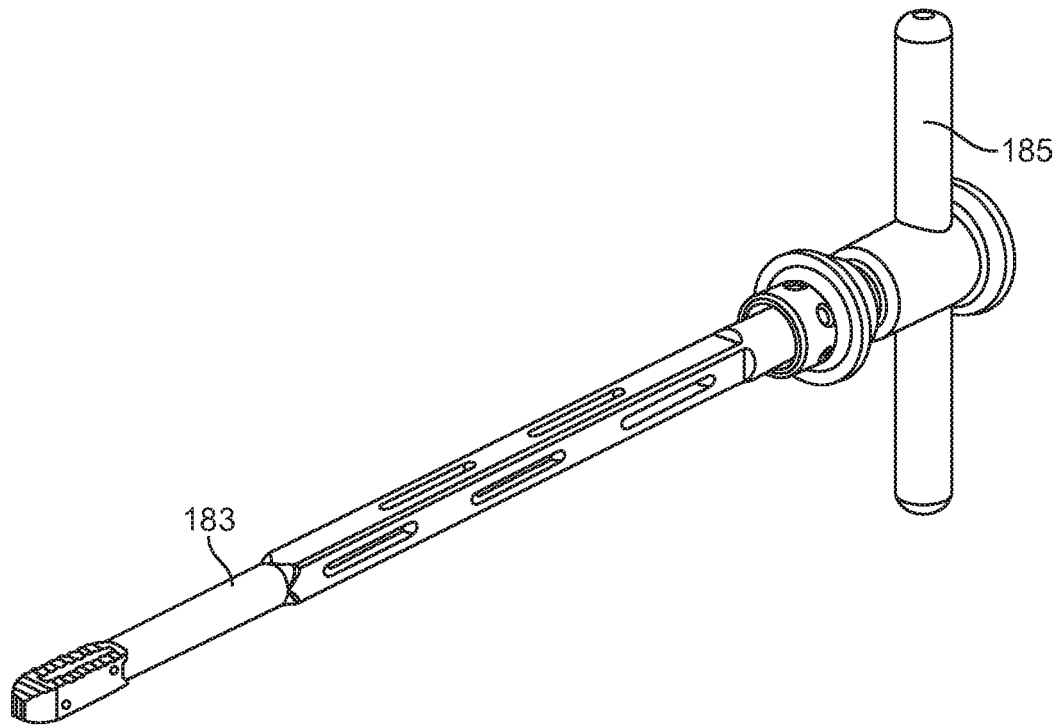

FIGS. 25A-25B illustrate an exemplary embodiment of an insertion tool that may be used in conjunction with the shims previously described above to deliver any of the interbody fusion devices described herein to a treatment site. Insertion instrument 183 includes an elongate shaft having a proximal end and distal end. A handle having a plurality of posts 185 extending radially outward forming a T-shaped handle is disposed on the proximal portion of the elongate shaft. The central portion of the shaft between the proximal and distal portions may be rectangular or square with cutouts passing through the wall of the shaft to lessen the weight of the device and also to permit an operator to see components passing through a central channel disposed in the shaft. The distal portion of the shaft may have a cylindrical portion. Insertion instrument 183 consists of a slot 184 that allows for engagement with the shims previously describe above such as shims 181 in FIG. 24A. The handle allows an operator to manipulate the insertion instrument, including rotating the instrument. Engagement feature 186 is configured to mate with the implant, such as rectangular end 22 in FIG. 1.

FIG. 25B illustrates the insertion instrument of FIG. 25A engaged with an interbody fusion device such as any of those described herein. The shims are coupled to the implant and they are disposed in the central channel of the elongate shaft.

Figure 26C:
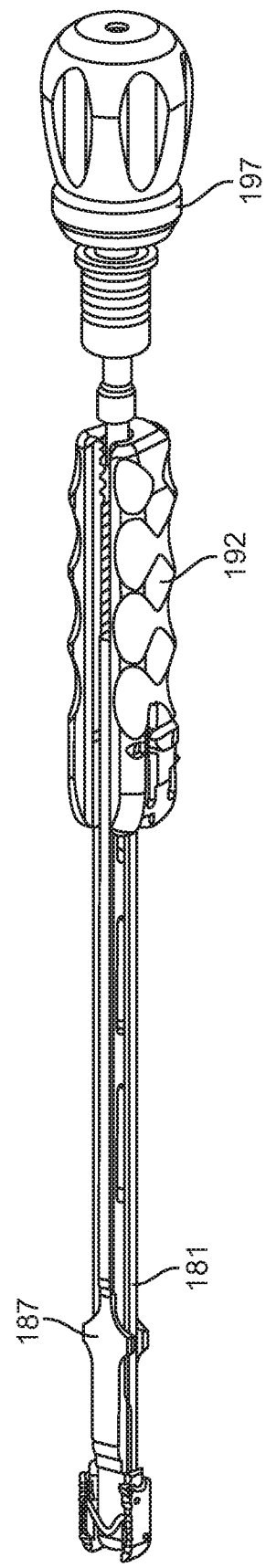

FIGS. 26A-26E illustrate various features of several embodiments of an expansion tool used to expand the implant from the collapsed configuration to the expanded or distracted configuration. FIG. 26A shows a perspective view of an expansion instrument 187. Expansion instrument 187 includes an elongate shaft having a proximal end and a distal end. Near the proximal end, slots 188 are configured to form a channel that engages the shims previously disclosed above. The elongate shaft includes a rectangular shaft 191 that may engage with a handle such as that seen in FIG. 26B and used during expansion of the implant. Expansion instrument 187 has angled surfaces 189 that form a tapered end for easier introduction between the elongated members of the implant. Threaded component 190 allows for controlled expansion of the implant.

FIG. 26B illustrates a perspective view of a handle that may be used with the expansion instrument in FIG. 26A. The handle includes a mating thread 193 to engage with threaded component 190, and rectangular slot 194 allows for translation of rectangular shaft 191 of expansion instrument 187 through the handle. Slot 196 allows for insertion of shim 181 and button 195 engages shim 181 with handle 192.

FIG. 26C illustrates a perspective view of the expansion instrument engaged with an implant. After the implant has been inserted into the intervertebral disc space, the insertion tool is removed, leaving the implant and shims in position. The shims and implant are then coupled to the expansion instrument as seen, and handle 192 and palm handle 197 are also attached to the expansion instrument. FIG. 26C shows the implant once expansion is complete. Shims 181 are shown engaged with the implant, expansion instrument 187, and handle 192. Expansion instrument 187 is also shown engaged with handle 192 and palm handle 197. Actuation of palm handle 197 by pushing it forward or distally is used to drive expansion instrument 187 between the elongated members of the implant to cause expansion thereof.

FIG. 26D highlights the engagement of the shim, expansion instrument and implant and shows expansion of the implant into the expanded configuration.

Figure 26E:
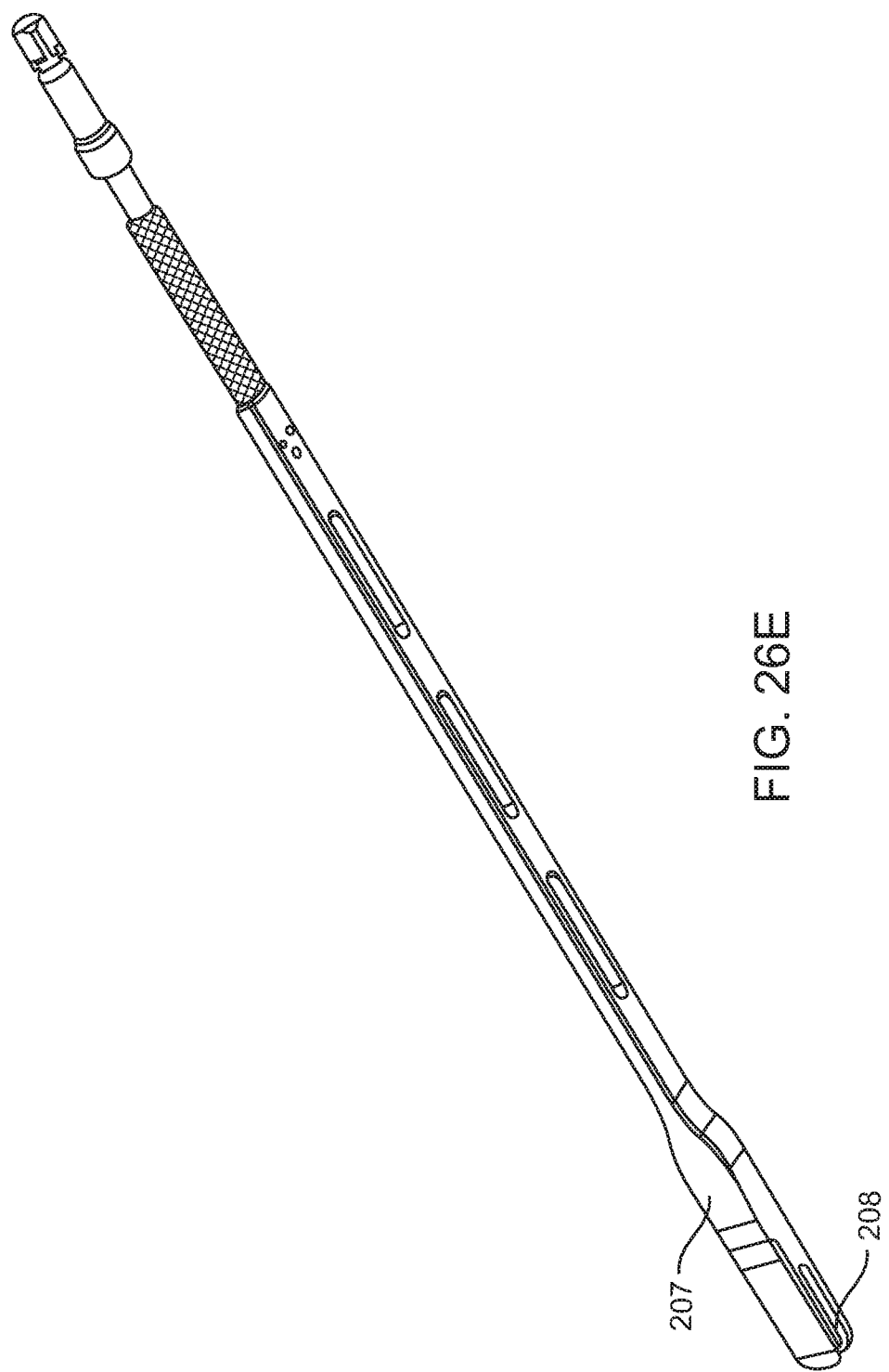

FIG. 26E illustrates a perspective view of an alternative embodiment of another expansion instrument 207. Expansion instrument 207 has a slot 208 to translate around centrally located spanning members.

FIGS. 28-32 more clearly illustrate use of the various instruments to insert and deploy the interbody implant. FIG. 28 shows the removal of insertion instrument 183 from the implant after the implant has been rotated 90 degrees, leaving shims 181 attached to the implant.

FIG. 29 shows the engagement of shims 181 with expansion instrument 187 and expansion handle 192. Shims 181 slide through slots 188 of expansion instrument 187 and slots 196 of expansion handle 192 where button 195 locks shims 181 in place.

Figure 30:
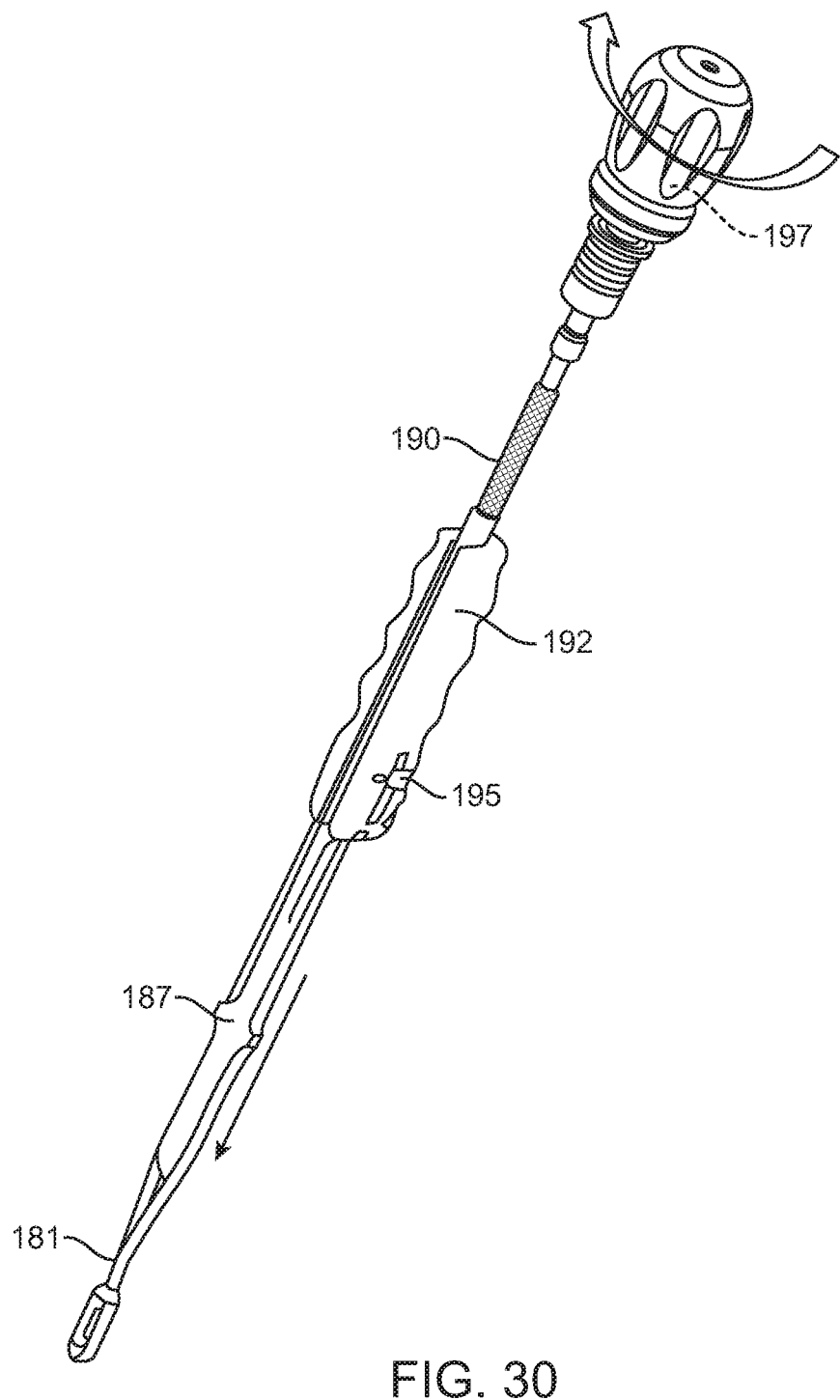
FIG. 30 illustrates a perspective view of the assembly in FIG. 29 with handle engagement.
Figure 31:
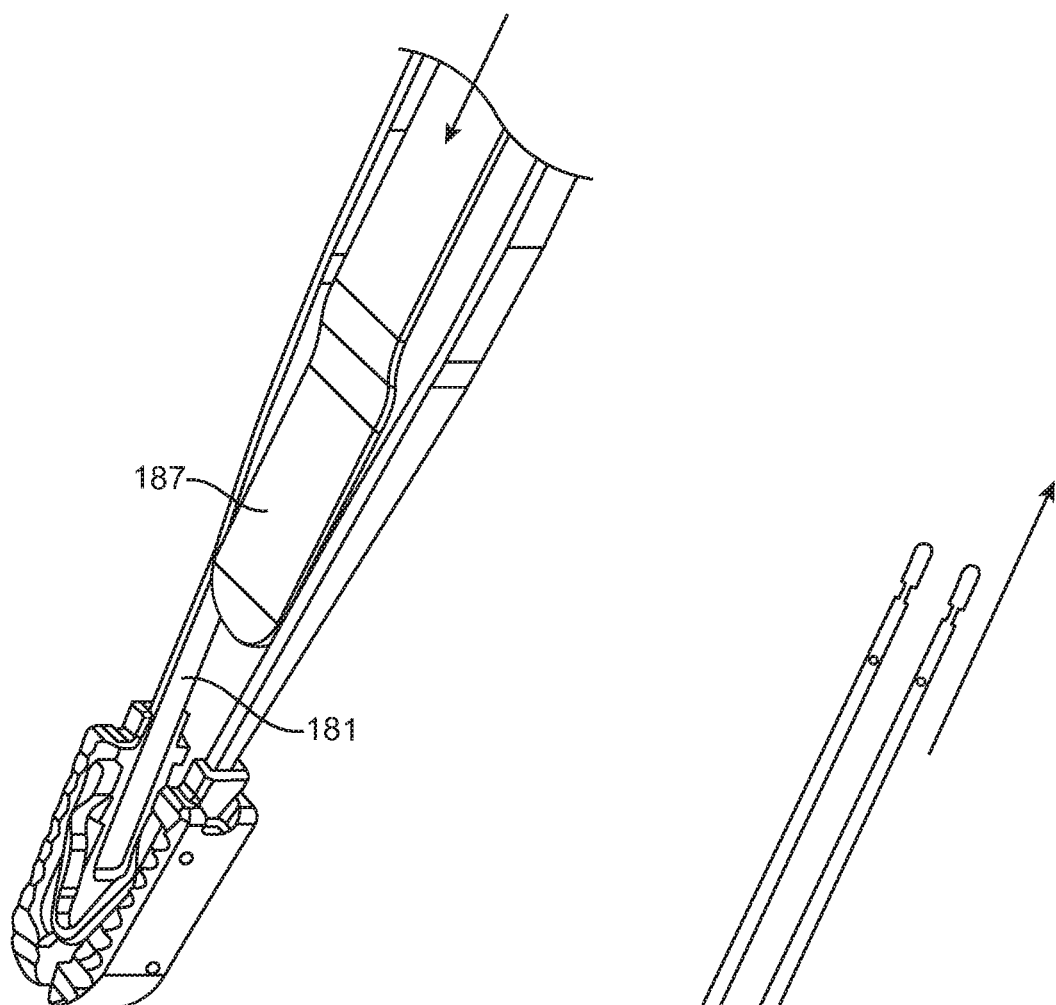
FIG. 31 illustrates a perspective view of the assembly in FIG. 30 during expansion.

FIG. 30 shows the engagement of handle 197 via a quick-connect. Expansion instrument 187 slides towards the implant until threaded component 190 engages with expansion handle 192. Handle 197 is then used to drive expansion instrument 187 towards the implant, separating shims 181 and thereby separating the elongated members of the implant as shown in FIG. 31. The final position of the expansion instruments can be seen in FIG. 26C. The expansion instruments can then be disengaged by driving component 190 away from the implant until threaded component 190 is no longer engaged with expansion handle 192. Pressing button 195 disengages shims 181, allowing the user to slide the expansion instruments away from the implant, leaving the expanded implant and shims 181 in place as shown in FIG. 32.

FIG. 31 shows expansion instrument 187 separating shims 181 and thereby separating the elongated members of the implant.

Figure 32:
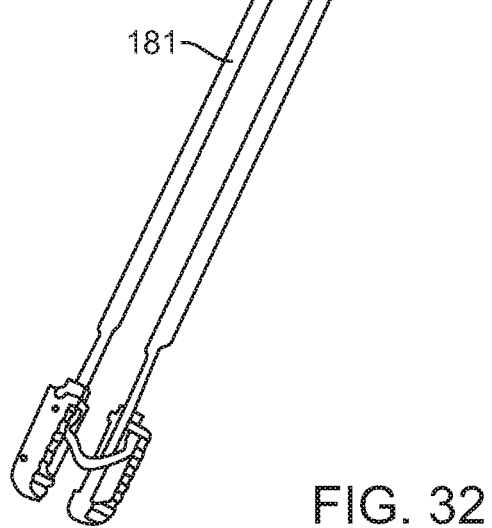
FIG. 32 illustrates a perspective view of the embodiment in FIG. 30 after the expansion instrument has been removed.

FIG. 32 shows shims 181 and the implant after expansion and after expansion instruments have been removed. Shims 181 can then be disengaged by pulling them away from the corresponding elongated member, leaving the implant in the expanded configuration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of deploying an interbody implant in an intervertebral space surrounded by adjacent vertebral bodies in a patient during a spinal fusion procedure, said method comprising:
   placing the interbody implant, formed from a plurality of elongated members, within the intervertebral space, said interbody implant having superior and inferior surfaces that have surface features to engage the adjacent vertebral bodies, wherein the vertebral bodies are configured to be engaged so as to distract the engaged vertebral bodies away from each other so as to increase the intervertebral space, and
   increasing a width between medial and lateral surfaces of the interbody implant from a first position having a first width to a second position having a second width by increasing a distance between at least two elongated members of the plurality of elongated members,
   wherein the plurality of elongated members are coupled together with one or more spanning components that deform when the width between medial and lateral surfaces of the interbody implant increases from the first position to the second position, and wherein the implant further comprises a pin that couples a spanning component of the one or more spanning components to an elongated member of the plurality of elongated members.

2. The method of claim 1, further comprising:

irreversibly increasing the width between medial and lateral surfaces of the interbody implant from the first position to the second position by deforming at least one deformation zone on the spanning component of the one or more spanning components.

3. The method of claim 1, wherein placing the interbody implant comprises placing the interbody implant into the intervertebral space in a first configuration such that medial and lateral surfaces of the interbody implant contact the vertebral bodies within the intervertebral space.

4. The method of claim 3, wherein placing the interbody implant comprises rotating the interbody implant from the first configuration to a second configuration such that superior and inferior surfaces of the interbody implant engage the vertebral bodies within the intervertebral space.

5. The method of claim 4, wherein rotating the interbody implant from the first configuration to the second configuration comprises rotating the interbody implant approximately 90 degrees between the first configuration and the second configuration.

6. The method of claim 2, wherein the at least one deformation zone is centrally located on the spanning component of the one or more spanning components.

7. The method of claim 6, wherein the spanning component of the one or more spanning components comprises a first leg and a second leg, and wherein a central portion of the spanning component of the one or more spanning components is disposed between the first and second legs of the spanning component of the one or more spanning components.

8. The method of claim 7, wherein the first and second legs of the spanning component of the one or more spanning components are substantially a same length.

9. The method of claim 7, wherein the first leg of the spanning component of the one or more spanning components has a free end, wherein at least one deformation zone is present at the free end of the first leg of the spanning component, and wherein the method further comprises deforming the at least one deformation zone at the free end of the first leg of the spanning component.

10. The method of claim 7, wherein the first and second legs of the spanning component of the one or more spanning components each have a free end, wherein at least one deformation zone is present at each free end of the first and second legs of the spanning component of the one or more spanning components, and wherein the method further comprises deforming the at least one deformation zone present at each free end of the first and second legs of the spanning component of the one or more spanning components.

* * * * *